United States Patent
de Smit et al.

(10) Patent No.: US 9,725,377 B2
(45) Date of Patent: *Aug. 8, 2017

(54) HYDROALKYLATION CATALYST AND PROCESS FOR USE THEREOF

(71) Applicant: ExxonMobil Chemical Patents Inc., Baytown, TX (US)

(72) Inventors: Emiel de Smit, Sint-Lambrechts-Woluwe (NL); Neeraj Sangar, League City, TX (US); Michael Salciccioli, Houston, TX (US); Jihad M. Dakka, Whitehouse Station, NJ (US); Lorenzo C. DeCaul, Langhorne, PA (US); Terry E. Helton, Bethlehem, PA (US); Scott J. Weigel, Allentown, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/314,557

(22) Filed: Jun. 25, 2014

(65) Prior Publication Data

US 2014/0378697 A1 Dec. 25, 2014

Related U.S. Application Data

(63) Continuation-in-part of application No. 14/201,287, filed on Mar. 7, 2014, and a continuation-in-part of application No. 14/201,224, filed on Mar. 7, 2014.

(Continued)

(51) Int. Cl.

| | |
|---|---|
| *C07C 69/76* | (2006.01) |
| *C07C 2/74* | (2006.01) |
| *C07C 51/265* | (2006.01) |
| *C07C 67/08* | (2006.01) |
| *C07C 5/367* | (2006.01) |
| *B01J 29/12* | (2006.01) |
| *B01J 29/22* | (2006.01) |
| *B01J 29/74* | (2006.01) |

(Continued)

(52) U.S. Cl.
CPC ............ *C07C 2/74* (2013.01); *B01J 29/088* (2013.01); *B01J 29/106* (2013.01); *B01J 29/12* (2013.01); *B01J 29/126* (2013.01); *B01J 29/146* (2013.01); *B01J 29/185* (2013.01); *B01J 29/22* (2013.01); *B01J 29/24* (2013.01); *B01J 29/7057* (2013.01); *B01J 29/7084* (2013.01); *B01J 29/7415* (2013.01); *B01J 29/7469* (2013.01); *B01J 29/7615* (2013.01); *B01J 29/7669* (2013.01); *C07C 5/367* (2013.01); *C07C 51/265* (2013.01); *C07C 67/08* (2013.01); *B01J 35/023* (2013.01); *B01J 35/026* (2013.01); *B01J 2029/081* (2013.01); *B01J 2229/186* (2013.01); *B01J 2229/42* (2013.01); *C07C 2521/12* (2013.01); *C07C 2529/08* (2013.01); *C07C 2529/12* (2013.01); *C07C 2529/22* (2013.01); *C07C 2529/74* (2013.01); *C07C 2529/80* (2013.01); *Y02P 20/52* (2015.11)

(58) Field of Classification Search
None
See application file for complete search history.

(56) References Cited

U.S. PATENT DOCUMENTS

| | | |
|---|---|---|
| 2,520,084 A | 8/1950 | Dazzi et al. |
| 2,634,248 A | 4/1953 | Dazzi |

(Continued)

FOREIGN PATENT DOCUMENTS

| | | |
|---|---|---|
| EP | 1 908 743 | 4/2008 |
| JP | 03-106833 A | 5/1991 |

(Continued)

OTHER PUBLICATIONS

Hoefnagel et al. Catalysis Letters vol. 85, Nos. 1-2, 2003.*

(Continued)

*Primary Examiner* — Sudhakar Katakam
*Assistant Examiner* — Ana Z Muresan

(57) ABSTRACT

This invention relates to process for producing biphenyl esters, the process comprising:

(a) contacting a feed comprising toluene, xylene or mixtures thereof with hydrogen in the presence of a hydroalkylation catalyst to produce a hydroalkylation reaction product comprising (methylcyclohexyl)toluene, wherein the hydroalkylation catalyst comprises: 1) binder present at 40 wt % or less (based upon weight of final catalyst composition), 2) a hydrogenation component present at 0.2 wt % or less (based upon weight of final catalyst composition), and 3) an acidic component comprising a molecular sieve having a twelve membered (or larger) ring pore opening, channel or pocket and a largest pore dimension of 6.0 angstroms or more present at 60 wt % or more, (based upon weight of final catalyst composition);

(b) dehydrogenating the hydroalkylation reaction product using a dehydrogenation catalyst to produce a dehydrogenation reaction product comprising a mixture of methyl-substituted biphenyl compounds;

(c) contacting at the dehydrogenation reaction product with an oxidizing gas to convert the methyl-substituted biphenyl compounds to biphenyl carboxylic acids; and (d) reacting the biphenyl carboxylic acids with one or more $C_1$ to $C_{14}$ alcohols to produce biphenyl esters.

21 Claims, 9 Drawing Sheets

Related U.S. Application Data

(60) Provisional application No. 61/781,129, filed on Mar. 14, 2013, provisional application No. 61/781,137, filed on Mar. 14, 2013.

(51) Int. Cl.
| | |
|---|---|
| *B01J 29/08* | (2006.01) |
| *B01J 29/10* | (2006.01) |
| *B01J 29/14* | (2006.01) |
| *B01J 29/18* | (2006.01) |
| *B01J 29/24* | (2006.01) |
| *B01J 29/70* | (2006.01) |
| *B01J 29/76* | (2006.01) |
| *B01J 35/02* | (2006.01) |

(56) References Cited

U.S. PATENT DOCUMENTS

| | | | |
|---|---|---|---|
| 2,976,266 | A | 3/1961 | Lytton et al. |
| 3,296,065 | A | 1/1967 | O'Brien et al. |
| 3,760,017 | A | 9/1973 | Arkell et al. |
| 3,842,040 | A * | 10/1974 | Browne et al. |
| 3,842,041 | A | 10/1974 | Browne et al. |
| 3,928,481 | A | 12/1975 | Suggitt |
| 3,928,484 | A | 12/1975 | Suggitt |
| 3,962,362 | A * | 6/1976 | Suggitt .................. 585/252 |
| 4,123,470 | A | 10/1978 | Murtha |
| 4,218,572 | A | 8/1980 | Dolhyj et al. |
| 4,263,457 | A | 4/1981 | Takeda et al. |
| 4,268,699 | A | 5/1981 | Murtha et al. |
| 4,294,976 | A | 10/1981 | Itatani et al. |
| 4,463,207 | A | 7/1984 | Johnson |
| 4,959,450 | A | 9/1990 | Morris et al. |
| 5,001,296 | A | 3/1991 | Howley et al. |
| 5,138,022 | A | 8/1992 | Mang et al. |
| 5,763,720 | A | 6/1998 | Buchanan et al. |
| 6,037,513 | A | 3/2000 | Chang et al. |
| 6,103,919 | A | 8/2000 | Schiraldi et al. |
| 6,274,756 | B1 | 8/2001 | Caers et al. |
| 6,355,711 | B1 | 3/2002 | Godwin et al. |
| 6,433,236 | B1 | 8/2002 | Schiraldi et al. |
| 6,482,972 | B1 | 11/2002 | Bahrmann et al. |
| 6,730,625 | B1 | 5/2004 | Chang et al. |
| 6,740,254 | B2 | 5/2004 | Zhou et al. |
| 6,777,514 | B2 | 8/2004 | Patil et al. |
| 7,297,738 | B2 | 11/2007 | Gosse et al. |
| 7,579,511 | B1 | 8/2009 | Dakka et al. |
| 8,217,213 | B2 | 7/2012 | Roth et al. |
| 8,829,093 | B2 | 9/2014 | Dakka et al. |
| 2005/0137437 | A1 | 6/2005 | Soloveichik et al. |
| 2005/0215433 | A1 | 9/2005 | Benitez et al. |
| 2006/0247461 | A1 | 11/2006 | Schlosberg et al. |
| 2008/0242895 | A1 | 10/2008 | Godwin et al. |
| 2009/0299111 | A1 * | 12/2009 | Kanbara et al. .................. 585/23 |
| 2010/0159177 | A1 | 6/2010 | Dakka et al. |
| 2011/0028762 | A1 | 2/2011 | Chen et al. |
| 2011/0151162 | A1 | 6/2011 | Dakka et al. |
| 2011/0184105 | A1 | 7/2011 | Dakka et al. |
| 2011/0215433 | A1 | 9/2011 | Kokubun |
| 2012/0108726 | A1 | 5/2012 | Godwin et al. |
| 2012/0108874 | A1 | 5/2012 | Gralla et al. |
| 2012/0283494 | A1 | 11/2012 | Smith et al. |
| 2014/0066663 | A1 | 3/2014 | Dakka et al. |
| 2014/0212666 | A1 | 7/2014 | Dakka et al. |
| 2014/0272626 | A1 | 9/2014 | Berlowitz et al. |
| 2014/0275605 | A1 | 9/2014 | Dakka et al. |
| 2014/0275606 | A1 | 9/2014 | Bai et al. |
| 2014/0275607 | A1 | 9/2014 | Dakka et al. |
| 2014/0275609 | A1 | 9/2014 | Dakka et al. |
| 2014/0315021 | A1 | 10/2014 | Naert et al. |
| 2014/0316155 | A1 | 10/2014 | Dakka et al. |
| 2014/0323782 | A1 | 10/2014 | Chen et al. |
| 2014/0378697 | A1 | 12/2014 | de Smit et al. |
| 2015/0080545 | A1 | 3/2015 | Dakka et al. |
| 2015/0080546 | A1 | 3/2015 | Dakka et al. |
| 2015/0361011 | A1 | 12/2015 | Salciccioli et al. |
| 2016/0115095 | A1 | 4/2016 | Dakka et al. |
| 2016/0176785 | A1 | 6/2016 | Salciccioli et al. |

FOREIGN PATENT DOCUMENTS

| | | |
|---|---|---|
| JP | 07-173086 A | 7/1995 |
| JP | 08-020548 | 1/1996 |
| JP | 08-099914 | 4/1996 |
| SU | 412182 | 1/1974 |
| WO | 94/08712 | 4/1994 |
| WO | WO 99/32427 | 7/1999 |
| WO | WO 03/029339 | 4/2003 |
| WO | WO 2004/046078 | 6/2004 |
| WO | WO 2007/013469 | 2/2007 |
| WO | WO 2009/128984 | 10/2009 |
| WO | WO 2010/138248 | 12/2010 |
| WO | WO 2011/096989 | 8/2011 |
| WO | WO 2011/096993 | 8/2011 |
| WO | WO 2012/082407 | 6/2012 |
| WO | WO 2012/134552 | 10/2012 |
| WO | WO 2012/157749 | 11/2012 |
| WO | WO 2014/159094 | 10/2014 |
| WO | WO 2014/159104 | 10/2014 |

OTHER PUBLICATIONS

U.S. Appl. No. 14/164,889, filed Jan. 27, 2013, Dakka et al.
U.S. Appl. No. 14/201,224, filed Mar. 7, 2014, Dakka et al.
U.S. Appl. No. 14/201,226, filed Mar. 7, 2013, Bai et al.
U.S. Appl. No. 14/201,284, filed Mar. 7, 2013, Dakka et al.
U.S. Appl. No. 14/201,287, filed Mar. 7, 2014, Dakka et al.
U.S. Appl. No. 61/781,129, filed Mar. 14, 2013, Dakka et al.
U.S. Appl. No. 61/781,137, filed Mar. 14, 2013, Dakka et al.
Cheng, J.C. et al., "Direct Alkylation of Aromatic Hydrocarbons with n-Paraffin", Mobil Technology Company, SRC Progress Memo 97-310-006, Dec. 1, 1997, pp. 1-43.
Clary et al., "*A Green, One-Pot Route to the Biphenyldicarboxylic Acids: Useful Intermediates in Polymer Synthesis*," International Journal of Organic Chemistry, Jun. 2013, vol. 3, No. 2, pp. 143-147.
Ennis et al., "*Multikilogram-Scale Synthesis of a Biphenyl Carboxylic Acid Derivative Using a Pd/C-Mediated Suzuki Coupling Approach,*" Organic Process 1999, 3(4), pp. 248-252.
Godwin, A.D. et al, "Plasticizers", Applied Polymer Science 21st Century, 2000, pp. 157-175.
Khromov et al., "*Catalytic Conversion of 1,1'-Dimethyldicyclohexyl and 1-Methyl-1-Phenyl-Cyclohexane on Platinum Catalysts at Elevated Hydrogen Pressures and Temperatures,*" Vestnik Moskovskogo Universiteta, Seriya 2: Khimiya (1965), 20(1), 51-5, (English Abstract Only).
Kulev, et al., "Esters of diphenic acid and their plasticizing properties", Izvestiya Tomskogo Politekhnicheskogo Instituta, 1961, 111. (English abstract only).
Lagidze et al., "*Analysis of Substances Produced by Reaction Between Aluminum Chloride and Diphenyl in Dearomatized Ligroin,*" V. 1. Leni-n Georgian Polytechnic Institute (1968), No. 2 (122), pp. 36-44. (English Translation).
Mukhopadhyay et al., "*Tandem One-Pot Palladium-Catalyzed Reductive and Oxidative Coupling of Benzene and Chlorobenzene,*" Journal of Organic Chemistry (2000), 65(10), pp. 3107-3110.
Shioda, et al., "*Synthesis of dialkyl diphenates and their properties*", Yuki Gosei Kaguku Kyokaishi, 1959, 17. (English abstract only).
Stevenson, S.A. et al., "*Conversion of Benzene to Phenylcyclohexane over a Tungsten/Zirconia Catalyst*", Mobil Technology Company, SRC Progress Memo 97M-0392, May 7, 1997, pp. 1-25.
Zhang, W. et al. "*Automation of Fluorous Solid-Phase Extraction for Parallel Synthesis*", J. Comb. Chem. (2006) pp. 890-896.
U.S. Appl. No. 61/040,480, filed Mar. 28, 2008, Godwin.
U.S. Appl. No. 61/203,626, filed Dec. 24, 2008, Dakka et al.
U.S. Appl. No. 61/577,900, filed Dec. 20, 2011, Dakka et al.
U.S. Appl. No. 61/781,109, filed Mar. 14, 2013, Dakka et al.
U.S. Appl. No. 61/781,116, filed Mar. 14, 2014, Bai et al.

(56) References Cited

OTHER PUBLICATIONS

U.S. Appl. No. 61/781,728, filed Mar. 14, 2014, Dakka et al.
U.S. Appl. No. 62/012,024, filed Jun. 13, 2014, Salciccioli et al.
U.S. Appl. No. 62/012,037, filed Jun. 13, 2014, Dakka et al.
U.S. Appl. No. 62/026,889, filed Jan. 27, 2015, Dakka et al.
U.S. Appl. No. 62/068,144, filed Oct. 24, 2014, Dakka et al.
U.S. Appl. No. 62/094,218, filed Dec. 19, 2014, Salciccioli et al.
U.S. Appl. No. 62/137,996, filed Mar. 25, 2015, Salciccioli et al.
U.S. Appl. No. 62/138,179, filed Mar. 25, 2015, Evans et al.
U.S. Appl. No. 62/140,723, filed Mar. 31, 2015, Salciccioli et al.
U.S. Appl. No. 13/316,745, filed Dec. 12, 2011, Patil et al.
U.S. Appl. No. 14/201,173, filed Mar. 7, 2014, Dakka et al.
U.S. Appl. No. 14/480,363, filed Sep. 8, 2014, Dakka et al.
U.S. Appl. No. 14/486,945, filed Sep. 15, 2014, Dobin et al.
U.S. Appl. No. 14/516,239, filed Oct. 16, 2014, Dakka et al.
U.S. Appl. No. 14/527,480, filed Oct. 29, 2014, Patil et al.
Bandyopadhyay et al., "*Transalkylation of cumene with toluene over zeolite Beta*," Applied Catalysis A: General, 1996, vol. 135(2), pp. 249-259.
Bandyopadhyay et al., "*Transalkylation reaction—An alternative route to produce industrially important intermediates such as cymene*," Catalysis Today, 1998, vol. 44, pp. 245-252.
Borodina et al., "Hydroalkylation of Benzene and Ethylbenzene over Metal-Containing Zeolite Catalysts," Petroleum Chemistry, 2009, vol. 49(1), pp. 66-73.
Guo, et al., "*Reactivity of 4,4'-Dimethylbiphenyl with Methanol over modified HZSM-5 Catalysts*," PrePrints—American Chemical Society, Division of Petroleum Chemistry, 2003, vol. 48(4), pp. 280-282.
Hoefnagel et al., "Selective alkylation of methylbenzenes with cyclohexene catalyzed by solid acids," Catalysis Letters, vol. 85, No. 1-2, 2003, pp. 7-11.
Izard, "Effect of Chemical Structure on Physical Properties of Isomeric Polyesters," Journal of Polymer Science, 1952, vol. 9(1), 35-39.
Krigbaum et al., "Aromatic Polyesters Forming Thermotropic Smectic Mesophases," Journal of Polymer Science, Part C, Polymer Letters Edition, 1982, vol. 20(2), pp. 109-115.
Lu et al., "Selective Hydrogenation of Single Benzene Ring in Biphenyl Catalyzed by Skeletal Ni," ChemCatChem., 2009, vol. 1(3), pp. 369-371.
Mavrodinova et al., "Transalkylation of toluene with cumene over zeolites Y dealuminated in solid-state, Part I. Effect of the alteration of Broensted acidity," Applied Catalysis A: General, 2003,vol. 248, pp. 181-196.
Mavrodinova et al., "Transalkylation of toluene with cumene over zeolites Y dealuminated in solid-state Part II. Effect of the introduced Lewis acid sites," Applied Catalysis A: General, 2003, vol. 248, p. 197-209.
Meurisse et al., "Polymers with Mesogenic Elements and Flexible Spacers in the Main Chain: Aromatic-Aliphatic Polyesters," British Polymer Journal, 1981, vol. 13(2), pp. 55-63.
Roux et al., "Critically Evaluated Thermochemical Properties of Polycyclic Aromatic Hydrocarbons," Journal of Physical and Chemical Reference Data, 2008, vol. 37(4), pp. 1855-1996.
Sherman et al., "Dimethylbiphenyls from toluene," American Chemical Society, Chemical Innovation, 2000, pp. 25-30.
Sinfelt, "The turnover frequency of methylcyclohexane dehydrogenation to toluene on a Pt reforming catalyst," Journal of Molecular Catalysis A: Chemical, 2000, vol. 163, pp. 123-128.
Sinfelt et al., "Kinetics of Methylcyclohexane Dehydrogenation Over Pt—$Al_2O_3$," Journal of Physical Chemistry, 1960, vol. 64(10), 1559-1562.
Singh, et. al, "*Studies on Isomer Distribution in the Products Obtained by Friedelcrafts Alkylation of Toluene with Cyclic Electrophiles*," National Academy Science Letters, 1983, vol. 6(10), pp. 321-325.
U.S. Appl. No. 14/976,983, filed Dec. 21, 2015, Salciccioli et al.
U.S. Appl. No. 62/320,014, filed Apr. 8, 2016, Dakka et al.
Depboylu, Can Okan, "An investigation of catalyst preparation conditions and promoter loading (Sn) effects on activity and selectivity of Pt catalyists in citral hydrogenation," Izmir Institute of Technology, Master Thesis, 2010, pp. 1-59.
Friedman, et al., "Alkylation of Benzene and Homologs with Methylcyclohexenes," Contributions from Sinclair Research Laboratories, Inc., 1957, vol. 79, pp. 1465-1468.
Kamiyama, T. et al., "Catalysts for the Hydroalkylation of Benzene, Toluene and Xylenes," Chem. Pharm. Bull., 1981, vol. 29(1), pp. 15-24.
Kovacic, Peter et al., "The Nature of the Methylcyclohexane-Ferric Chloride Reaction," The Journal of Organic Chemistry, Oct. 1963, vol. 28, No. 10, pp. 2551-2554.
Sherman, Christopher S. et al., "Isomerization of Substituted Biphenyls by Superacid. A remarkable Confluence of Experiment and Theory," The Journal of Organic Chemistry, Mar. 8, 2002, vol. 67,No. 7, pp. 2034-2041.
Sherman, S. Christopher et al., "Supplementary Information for: Isomerisation of Substituted Biphenyls by Superacid. A remarkable Confluence of Experiment and Theory," The Journal of Organic Chemistry, Mar. 8, 2002, pp. 1-40.
Smirnitsky, V. I. et al., "Hydrodimerization of benzene and alkylbenzene over polyfunctional zeolite catalysts," Studies in Surface Science and Catalysis, Jan. 1, 1994, vol. 84, pp. 1813-1820.

\* cited by examiner

HYDROALKYLATION CATALYST AND PROCESS FOR USE THEREOF

PRIORITY

This application is a continuation in part of U.S. Ser. No. 14/201,287, filed Mar. 7, 2014, which claims the benefit of and priority to U.S. Ser. No. 61/781,129, filed Mar. 14, 2013.

This application is also a continuation in part of U.S. Ser. No. 14/201,224, filed Mar. 7, 2014 which claims the benefit of and priority to U.S. Ser. No. 61/781,137, filed Mar. 14, 2013.

FIELD OF THE INVENTION

This invention relates to hydroalkylation catalysts comprising selected zeolites combined with hydrogenation catalysts and processes using such catalysts.

BACKGROUND OF THE INVENTION

The development of plasticizers from low cost petrochemical feedstock is of interest to the polyvinyl chloride industry. A candidate for a general purpose plasticizer is the biphenylester family of molecules. Dimethylbiphenyl DMBP is an intermediate in the process to make these plasticizer molecules. Plasticizers are incorporated into a resin (usually a plastic or elastomer) to increase the flexibility, workability, etc. of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Useful plasticizers include those based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, U.S. Patent Publication No. 2006-0247461, and U.S. Pat. No. 7,297,738.

Other useful plasticizers include esters based on benzoic acid (see, for instance, U.S. Pat. No. 6,740,254) and polyketones, such as described in U.S. Pat. No. 6,777,514; and U.S. Patent Publication No. 2008-0242895. Epoxidized soybean oil, which has much longer alkyl groups ($C_{16}$ to $C_{18}$), has been tried as a plasticizer, but is generally used as a PVC stabilizer. Stabilizers are used in much lower concentrations than plasticizers. U.S. Patent Publication No. 2010-0159177 discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins and that can be made with a high throughput.

Typically, the best that has been achieved with the above are flexible PVC articles having either reduced performance or poorer processability. Thus, existing efforts to make plasticizer systems for PVC have not proven to be entirely satisfactory, and so this is still an area of intense research.

For example, in an article entitled "Esters of diphenic acid and their plasticizing properties", Kulev et al., *Izvestiya Tomskogo Politekhnicheskogo Instituta* (1961) 111, disclose that diisoamyl diphenate, bis(2-ethylhexyl)diphenate and mixed heptyl, octyl and nonyl diphenates can be prepared by esterification of diphenic acid, and allege that the resultant esters are useful as plasticizers for vinyl chloride. Similarly, in an article entitled "Synthesis of dialkyl diphenates and their properties", Shioda et al., *Yuki Gosei Kagaku Kyokaishi* (1959), 17, disclose that dialkyl diphenates of $C_1$ to $C_8$ alcohols, said to be useful as plasticizers for poly(vinyl chloride), can be formed by converting diphenic acid to diphenic anhydride and esterifying the diphenic anhydride. However, since these processes involve esterification of diphenic acid or anhydride, they necessarily result in 2,2'-substituted diesters of diphenic acid. Generally, such diesters having substitution on the 2-carbons have proven to be too volatile for use as plasticizers.

An alternative method of producing dialkyl diphenate esters having an increased proportion of the less volatile 3,3', 3,4' and 4,4' diesters has now been developed. In particular, it has been found that dimethylbiphenyl compounds containing significant amounts of the 3,3'-dimethyl, the 3,4'-dimethyl and the 4,4'-dimethyl isomers can be economically produced by hydroalkylation of toluene and/or xylene followed by dehydrogenation of the resulting (methylcyclohexyl)toluene and/or (dimethylcyclohexyl)xylene product. The resultant mixture can be used as a precursor in the production of biphenylester-based plasticizers by, for example, oxidizing the methyl-substituted biphenyl compounds to convert at least one of the methyl groups to a carboxylic acid group and then esterifying the carboxylic acid group with an alcohol, such as an OXO-alcohol. In addition, depending on the catalyst employed, the hydroalkylation reaction exhibits low selectivity to fully saturated compounds, which are difficult to dehydrogenate to biphenyls, and low selectivity to heavies, which must be removed resulting in yield loss.

The production of biphenylesters is based on the initial steps of aromatic hydroalkylation (see U.S. Ser. No. 14/201, 226, U.S. Ser. No. 14/201,287, and U.S. Ser. No. 14/201, 224, filed Mar. 7, 2013), followed by dehydrogenation to produce biphenyls or alkylbiphenyls (see U.S. Ser. No. 14/164,889, filed Jan. 27, 2013, U.S. Ser. No. 14/201,287, and U.S. Ser. No. 14/201,284, filed Mar. 7, 2013).

Additional references of interest include U.S. Pat. No. 6,103,919.

SUMMARY OF THE INVENTION

A process for producing (methylcyclohexyl)toluene, the process comprising:

(a) contacting a feed comprising toluene, xylene or mixtures thereof with hydrogen in the presence of a hydroalkylation catalyst under conditions effective to produce a hydroalkylation reaction product comprising (methylcyclohexyl)toluene, wherein the hydroalkylation catalyst comprises: 1) binder present at 40 wt % or less, 2) a hydrogenation component present at 0.2 wt % or less, and 3) an acidic component comprising a molecular sieve having a twelve membered (or larger) ring pore opening, channel or pocket and a largest pore dimension of 6.0 angstroms or more present at 60 wt % or more, (each based upon weight of final catalyst composition).

DETAILED DESCRIPTION

Figure 1:
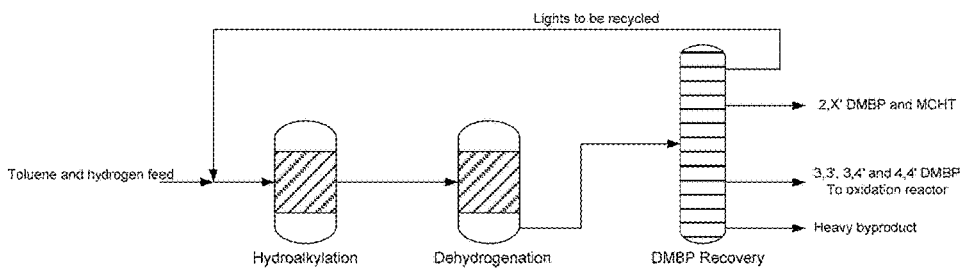
FIG. 1 is a simplified process scheme for dimethylbiphenyl production. 3,3', 3,4' and 4,4' DMBP isomers are recovered for oxidation. Remaining stream contains 2,X' DMBP isomers and unreacted methylcyclohexyltoluene.

All numerical values within the detailed description and the claims herein are modified by "about" or "approximately" the indicated value, and take into account experimental error and variations that would be expected by a person having ordinary skill in the art.

As used herein, the numbering scheme for the Periodic Table Groups is as disclosed in Chemical and Engineering News, 63(5), 27 (1985).

Unless otherwise indicated, room temperature is about 23° C.

The following abbreviations are used herein: MCH is methylcyclohexane, MCHT is methylcyclohexyltoluene, the abbreviation x,y-MCHT refers to x-y-methylcyclohexyltoluene where x=ortho, meta or para and y=1, 2, 3 or 4, DMBP is dimethylbiphenyl, DMBCH is dimethylbicyclohexane, ECP-Toluene is used to describe o-(2-ethylcyclopent-1-enyl)-toluene, p-(2-ethylcyclopent-1-enyl)-toluene, dimethylcyclopentenyl-toluene and similar molecules containing a 5-ring.

There is an increased interest in developing new plasticizers which possess good plasticizer performance characteristics but are still competitive economically. The present disclosure is directed towards production of ester or diester plasticizers that can be made from low cost feeds and employ fewer manufacturing steps in order to meet economic targets, and catalysts which show high activity, high selectivity to MCHT at high conversion and high selectivity to desired MCHT isomers (m,3-MCHT, m,4-MCHT, p,3-MCHT, p,4-MCHT, where m=meta and p=para) while minimizing selectivity to light molecules, i.e. methylcyclohexane, dimethylbicyclohexane, $C_{15+}$ molecules and other undesired isomers, such as those having an alkyl group at the 1 position. The desired MCHT is then dehydrogenated to dimethyl biphenyl, which in turn can be oxidized to a mono or dicarboxylic acid biphenyl, which in turn is esterified to a mono or diester biphenyl.

The present disclosure also relates to the production of methyl substituted biphenyl compounds by the catalytic hydroalkylation of toluene and/or xylene followed by dehydrogenation of at least part of the hydroalkylation reaction product. Depending on the catalyst employed in the hydroalkylation reaction, the hydroalkylation process is selective to the production of the desired (methylcyclohexyl)toluenes and/or (dimethylcyclohexyl)xylenes without excessive production of heavies and fully saturated rings. In addition, the dimethylbiphenyl product of the dehydrogenation reaction contains significant amounts of the 3,3'-dimethyl, the 3,4'-dimethyl and the 4,4'-dimethyl compounds making the product an attractive precursor in the production of biphenylester-based plasticizers.

In another aspect, the present disclosure is directed to a process for producing methyl-substituted biphenyl compounds, the process comprising:

(a) contacting a feed comprising at least one aromatic hydrocarbon selected from the group consisting of benzene, toluene, xylene and mixtures thereof with hydrogen in the presence of a hydroalkylation catalyst under conditions effective to produce a hydroalkylation reaction product comprising (methylcyclohexyl)benzenes and/or (cyclohexyl)toluenes and/or (dimethylcyclohexyl)benzenes and/or (cyclohexyl)xylenes and/or (methylcyclohexyl)toluenes and/or (dimethylcyclohexyl)xylenes; and (b) dehydrogenating at least part of the hydroalkylation reaction product in the presence of a dehydrogenation catalyst under conditions effective to produce a dehydrogenation reaction product comprising a mixture of methyl-substituted biphenyl compounds, wherein the hydroalkylation catalyst comprises: 1) binder present at 40 wt % or less (based upon weight of final catalyst composition), 2) a hydrogenation component present at 0.2 wt % or less (based upon weight of final catalyst composition), and 3) an acidic component comprising a molecular sieve having a twelve membered (or larger) ring pore opening, channel or pocket and a largest pore dimension of 6.0 angstroms or more present at 60 wt % or more, (based upon weight of final catalyst composition).

In another aspect, the present disclosure is directed to a process for producing biphenyl esters, the process comprising:

(a) contacting a feed comprising at least one aromatic hydrocarbon selected from the group consisting of toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes;

(b) dehydrogenating at least part of the hydroalkylation reaction product in the presence of a dehydrogenation catalyst under conditions effective to produce a dehydrogenation reaction product comprising a mixture of methyl-substituted biphenyl compounds;

(c) contacting at least part of the dehydrogenation reaction product with an oxidizing gas under conditions effective to convert at least part of the methyl-substituted biphenyl compounds to biphenyl carboxylic acids; and (d) reacting the biphenyl carboxylic acids with one or more $C_4$ to $C_{14}$ alcohols under conditions effective to produce biphenyl esters;

wherein the hydroalkylation catalyst comprises: 1) binder present at 40 wt % or less (based upon weight of final catalyst composition), 2) a hydrogenation component present at 0.2 wt % or less (based upon weight of final catalyst composition), and 3) an acidic component comprising a molecular sieve having a twelve membered (or larger) ring pore opening, channel or pocket and a largest pore dimension of 6.0 angstroms or more present at 60 wt % or more, (based upon weight of final catalyst composition).

In yet another aspect, the present disclosure is directed to a process for producing (methylcyclohexyl)toluene, the process comprising:

(a) contacting a feed comprising toluene, xylene and mixtures thereof (preferably toluene) with hydrogen in the presence of a hydroalkylation catalyst under conditions effective to produce a hydroalkylation reaction product comprising (methylcyclohexyl)toluene, wherein the hydroalkylation catalyst comprises: 1) binder present at 40 wt % or less (based upon weight of final catalyst composition), 2) a hydrogenation component present at 0.2 wt % or less (based upon weight of final catalyst composition), and 3) an acidic component comprising a molecular sieve having a twelve membered (or larger) ring pore opening, channel or pocket and a largest pore dimension of 6.0 angstroms or more present at 60 wt % or more, (based upon weight of final catalyst composition).

This invention further relates to catalysts which show high activity, high selectivity to MCHT at high conversion and high selectivity to desired MCHT isomers (m,3-MCHT, m,4-MCHT, p,3-MCHT, p,4-MCHT) while minimizing selectivity to light molecules, methylcyclohexane, dimethylbicyclohexane, $C_{15+}$ molecules and other undesired isomers, particularly MCHT isomers having a methyl group at the benzylic position (also referred to as the 1 position).

In yet another aspect, the present disclosure is directed to a process for producing (methylcyclohexyl)toluene, the process comprising:

(a) contacting a feed comprising toluene with hydrogen in the presence of a hydroalkylation catalyst under conditions effective to produce a hydroalkylation reaction product comprising (methylcyclohexyl)toluene, wherein the hydroalkylation catalyst comprises: 1) binder present at 40 wt % or less, based upon weight of final catalyst composition (preferably from 0.05 to 30 wt %, preferably from 0.1 to 25 wt %, preferably 1 to 20 wt %); 2) one or more hydrogenation components present at 0.2 wt % or less, based upon weight of final catalyst composition (preferably from 0.01 to 0.2 wt %, preferably 0.05 to 0.2 wt %, preferably 0.1 to 0.2 wt %); and 3) one or more acidic components comprising a molecular sieve having a twelve membered (or larger) ring pore opening, channel or pocket and a largest pore dimension of 6.0 angstroms or more present at 60 wt % or more, based upon weight of final catalyst composition (preferably 70 wt % or more, preferably from 80 to 99 wt %, preferably 85 to 95 wt %).

In one aspect, the present disclosure is directed to a process for producing methyl-substituted biphenyl compounds, the process comprising:

(a) contacting a feed comprising at least one aromatic hydrocarbon comprising one or more of (preferably selected from the group consisting of) toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes; and (b) dehydrogenating at least part of the hydroalkylation reaction product in the presence of a dehydrogenation catalyst under conditions effective to produce a dehydrogenation reaction product comprising a mixture of methyl-substituted biphenyl compounds;

wherein the hydroalkylation catalyst comprises: 1) binder present at 40 wt % or less (based upon weight of final catalyst composition), preferably 0.05 to 30 wt %, preferably 0.1 to 25 wt %, preferably 1 to 20 wt %, 2) one or more hydrogenation components present at 0.2 wt % or less (based upon weight of final catalyst composition) preferably from 0.01 to 0.2 wt %, preferably 0.05 to 0.2 wt %, preferably 0.1 to 0.2 wt %, and 3) one or more acidic components comprising a molecular sieve having a twelve membered (or larger) ring pore opening, channel or pocket and a largest pore dimension of 6.0 angstroms or more present at 60 wt % or more, (based upon weight of final catalyst composition) preferably 70 wt % or more, preferably from 80 to 99 wt %, preferably 85 to 95 wt %.

In another aspect, the present disclosure is directed to a process for producing biphenyl carboxylic acids, the process comprising:
  (a) contacting a feed comprising at least one aromatic hydrocarbon comprising one or more of (preferably selected from the group consisting of) toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes;
  (b) dehydrogenating at least part of the hydroalkylation reaction product in the presence of a dehydrogenation catalyst under conditions effective to produce a dehydrogenation reaction product comprising a mixture of methyl-substituted biphenyl compounds;
  (c) contacting at least part of the dehydrogenation reaction product with an oxidizing gas under conditions effective to convert at least part of the methyl-substituted biphenyl compounds to biphenyl carboxylic acids;
  wherein the hydroalkylation catalyst comprises: 1) binder present at 40 wt % or less (based upon weight of final catalyst composition), preferably 30 wt % or less, preferably from 0.1 to 25 wt %, preferably 1 to 20 wt %, 2) one or more hydrogenation components present at 0.2 wt % or less (based upon weight of final catalyst composition) preferably from 0.01 to 0.2 wt %, preferably 0.05 to 0.2 wt %, preferably 0.1 to 0.2 wt %, and 3) one or more acidic components comprising a molecular sieve having a twelve membered (or larger) ring pore opening, channel or pocket and a largest pore dimension of 6.0 angstroms or more present at 60 wt % or more, (based upon weight of final catalyst composition) preferably 70 wt % or more, preferably from 80 to 99 wt %, preferably 85 to 95 wt %.

In another aspect, the present disclosure is directed to a process for producing biphenyl esters, the process comprising:
  (a) contacting a feed comprising at least one aromatic hydrocarbon comprising one or more of (preferably selected from the group consisting of) toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes;
  (b) dehydrogenating at least part of the hydroalkylation reaction product in the presence of a dehydrogenation catalyst under conditions effective to produce a dehydrogenation reaction product comprising a mixture of methyl-substituted biphenyl compounds;
  (c) contacting at least part of the dehydrogenation reaction product with an oxidizing gas under conditions effective to convert at least part of the methyl-substituted biphenyl compounds to biphenyl carboxylic acids; and
  (d) reacting the biphenyl carboxylic acids with one or more $C_4$ to $C_{14}$ alcohols under conditions effective to produce biphenyl esters;
  wherein the hydroalkylation catalyst comprises: 1) binder present at 40 wt % or less (based upon weight of final catalyst composition), preferably 0.05 to 30 wt %, preferably from 0.1 to 25 wt %, preferably 1 to 20 wt %, 2) one or more hydrogenation components present at 0.2 wt % or less (based upon weight of final catalyst composition) preferably from 0.01 to 0.2 wt %, preferably 0.05 to 0.2 wt %, preferably 0.1 to 0.2 wt %, and 3) one or more acidic components comprising a molecular sieve having a twelve membered (or larger) ring pore opening, channel or pocket and a largest pore dimension of 6.0 angstroms or more present at 60 wt % or more, (based upon weight of final catalyst composition) preferably 70 wt % or more, preferably from 80 to 99 wt %, preferably 85 to 95 wt %.

Hydroalkylation Catalyst

In a preferred embodiment of the invention, the hydroalkylation catalyst comprises one or more binders, one or more hydrogenation components and one or more acidic components.

Binder

In a preferred embodiment of the invention, the catalyst includes one or more binders such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, perovskite, spinel, lanthanide oxides, and transition metal oxides. Preferred binders include pseudoboehmite alumina, alumina, silica, titania and mixtures thereof.

Hydrogenation Component

Any known hydrogenation metal or compound thereof can be employed as the hydrogenation component(s) of the catalyst, although suitable metals include platinum, palladium, ruthenium, rhenium, rhodium, nickel, zinc, tin, and cobalt, with palladium being particularly advantageous. In certain embodiments, the amount of hydrogenation metal present in the catalyst is present at about 0.05 to about 10 wt %, such as about 0.1 to about 5 wt %, of the catalyst. In an alternate embodiment, the hydrogenation components present in the catalyst are present at 0.2 wt % or less (based upon weight of final catalyst composition) preferably from 0.01 to 0.2 wt %, preferably 0.05 to 0.2 wt %, preferably 0.1 to 0.2 wt %.

Acidic Component

In one embodiment, the solid acid alkylation component comprises a large pore molecular sieve having molecular sieve having a twelve membered (or larger) ring pore opening, channel or pocket or larger and a largest pore dimension of 6.0 angstroms or more, preferably 6.9 angstroms or more. The molecular sieve may be present at 60 wt % or more, (based upon weight of final catalyst composition) preferably 70 wt % or more, preferably from 80 to 99 wt %, preferably 85 to 95 wt %.

Largest pore dimension means the larger of the width or the length when measuring a pore, as reported by the *Atlas of Zeolite Framework Types* (Baerlocher, McCusker, Olson, 6th revised edition, 2007) or from the website maintained by the Structure Commission of the International Zeolite Association (IZA-SC), or its successor (http://www.iza-structure.org/databases/), in event of conflict, the *Atlas of Zeolite Framework Types* (Baerlocher, McCusker, Olson, 6th revised edition, 2007 shall control. The numbers in the atlas are the crystallographic free diameters of the channel designated as the effective pore width. The pore width is based upon the atomic coordinates of the type material and an oxygen radius of 1.35 A.

Suitable large pore, channel or pocket molecular sieves include MWW, zeolite beta, zeolite Y, Ultrastable Y (USY), Dealuminated Y (DeAl Y), mordenite, ZSM-2, ZSM-3, ZSM-4 (including mazzite, omega, and intergrowths with mordenite), ZSM-10, ZSM-12, ZSM-18, zeolite L, SAPO-5, SAPO-37, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminated Y zeolite (DeAl Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

In a useful embodiment, the molecular sieve is selected from the FAU, MOR, MWW, BEA, and MTW families, preferably the FAU, MWW, and MOR families.

In a useful embodiment, the molecular sieve is an acidic, porous material that contains 12-membered (or larger) rings or where the largest dimension of the pore opening is 6.0 angstroms or larger. The porous material can be amorphous or crystalline and typically comprises at least one of Si, Al, O, H, P, Ga, B, Zn, Ge, and C. Particularly useful porous materials include aluminosilicates and silicoaluminophosphates.

In a useful embodiment, the porous material comprises micropores, mesopores, or macropores (micropores are smaller than 2 nm, mesopores are 2 nm to 50 nm, macropores are greater than 50 nm).

Useful aluminosilicates include boggsite, CIT-1, hexagonal faujasites, zeolite L, mazzite (ZSM-4), ZSM-10, ZSM-18, faujasite, mordenite (note: faujasite includes zeolite Y and USY) or mixtures thereof, preferably the acidic component comprises a molecular sieve selected from the group consisting of faujasite (such as cubic faujasite, hexagonal faujasite, zeolite Y, Ultrastable Y (USY), Dealuminated Y (Deal Y)), mordenite, SAPO, zeolite L, zeolite Beta and Mordenite.

In a preferred embodiment, the molecular sieve has a Constraint Index (as defined in U.S. Pat. No. 4,016,218) of less than 2.

In another embodiment, the molecular sieves useful herein do not have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system.

In another embodiment, the molecular sieves useful herein are not members of the MCM-22 family. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

In particularly useful embodiments, the acidic component comprises a molecular sieve selected from the group consisting of ZSM-12, zeolite Beta, faujasite (zeolite Y, Ultrastable Y (USY), Dealuminated Y (Deal Y)), mordenite; the hydrogenation component is palladium, ruthenium, nickel, zinc, tin, and cobalt, with palladium being particularly advantageous; and the binder is selected from pseudoboehmite alumina, alumina, silica, titania and mixtures thereof.

In a particularly useful embodiment, the catalyst comprises Pd on mordenite/alumina (such as 0.15 wt % Pd on 65-80 wt % mordenite/20-35 wt % boehmite alumina, or 0.15 wt % Pd on 65-80 wt % USY/20-35 wt % boehmite alumina)

Hydroalkylation of Toluene and/or Xylene

Hydroalkylation is a two-stage catalytic reaction in which an aromatic compound is partially hydrogenated to produce a cyclic olefin, which then reacts, in situ, with the aromatic compound to produce a cycloalkylaromatic product. In the present process, the aromatic compound comprises toluene and/or xylene and the cycloalkylaromatic product comprises a mixture of (methylcyclohexyl)toluene and/or (dimethylcyclohexyl)xylene isomers. In the case of toluene, the desired reaction may be summarized as follows:

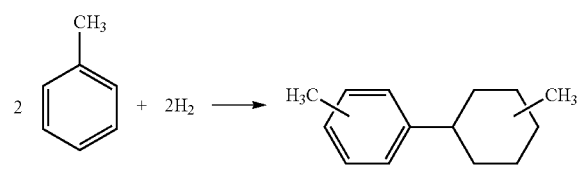

Among the competing reactions is further hydrogenation of the cyclic olefin intermediate and/or the cycloalkylaromatic product to produce fully saturated rings. In the case of toluene as the hydroalkylation feed, further hydrogenation can produce methylcyclohexane and dimethylbicyclohexane compounds. Although these by-products can be converted back to feed (toluene) and to the product ((methylcyclohexyl)toluene and dimethylbiphenyl) via dehydrogenation, this involves an endothermic reaction requiring high temperatures (greater than 350° C.) to obtain high conversion. This not only makes the reaction costly but can also lead to further by-product formation and hence yield loss. It is therefore desirable to employ a hydroalkylation catalyst that exhibits low selectivity towards the production of fully saturated rings.

Another competing reaction is dialkylation in which the (methylcyclohexyl)toluene product reacts with further methylcyclohexene to produce di(methylcyclohexyl)toluene. Again this by-product can be converted back to (methylcyclohexyl)toluene, in this case by transalkylation. However, this process requires the use of an acid catalyst at temperatures above 160° C. and can lead to the production of additional by-products, such as di(methylcyclopentyl)toluenes, cyclohexylxylenes and cyclohexylbenzene. It is therefore desirable to employ a hydroalkylation catalyst that exhibits low selectivity towards di(methylcyclohexyl)toluene and other heavy by-products.

In addition to the toluene and/or xylene and hydrogen, a diluent, which is substantially inert under hydroalkylation conditions, may be included in the feed to the hydroalkylation reaction. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane, methylcyclohexane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

In one embodiment, the aromatic feed to the hydroalkylation reaction also includes benzene and/or one or more alkylbenzenes different from toluene and xylene. Suitable alkylbenzenes may have one or more alkyl groups with up to 4 carbon atoms and include, by way of example, ethylbenzene, cumene, and unseparated $C_6$-$C_8$ or $C_7$-$C_8$ or $C_7$-$C_9$ streams.

The hydroalkylation reaction can be conducted in a wide range of reactor configurations including fixed bed (single or in series), slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. The molar ratio of hydrogen to aromatic feed is typically from about 0.15:1 to about 15:1.

In the present process, it is found that FAU, MOR, MWW, BEA, and MTW families of molecular sieves are particularly active and stable catalysts for the hydroalkylation of toluene or xylene. In addition, catalysts containing FAU, MWW, and MOR families of molecular sieves exhibit improved selectivity to the 3,3'-dimethyl, the 3,4'-dimethyl, the 4,3'-dimethyl and the 4,4'-dimethyl isomers for the biphenyl and the MCHT precursors (particularly m,3-MCHT, m,4-MCHT, p,3-MCHT and p,4-MCHT) in the hydroalkylation product, while at the same time reducing the formation of fully saturated and heavy by-products. For example, using a molecular sieve described herein with a toluene feed, it is found that the hydroalkylation reaction product may comprise:

1) at least 60 wt %, such as at least 70 wt %, for example at least 75 wt % of the 3,3, 3,4, 4,3 and 4,4-isomers (also referred to as the m,3, m,4, p,3 and p,4-isomers) of (methylcyclohexyl)toluene based on the total weight of all the (methylcyclohexyl)toluene isomers;
2) less than 30 wt % of methylcyclohexane and less than 2% of dimethylbicyclohexane compounds; and
3) less than 1 wt % of compounds containing in excess of 14 carbon atoms.

Similarly, with a xylene feed, the hydroalkylation reaction product may comprise less than 1 wt % of compounds containing in excess of 16 carbon atoms.

By way of illustration, the 3,3', 3,4', 4,3' and 4,4' (also referred to as the m,3, m,4 p,3 and p,4-isomers)-isomers of (methylcyclohexyl)toluene are illustrated in formulas F1 to F4, respectively:

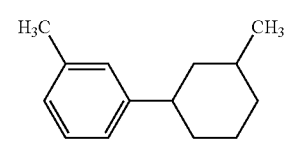

F1

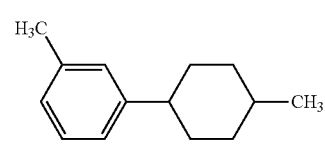

F2

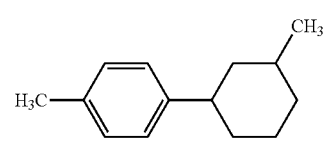

F3

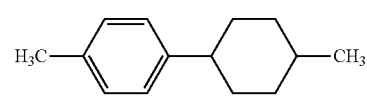

F4

In contrast, when the methyl group is located in the 1-position, also referred to as the benzylic position (which forms a quaternary carbon) on the cyclohexyl ring, ring isomerization can occur forming (dimethylcyclopentenyl)toluene and (ethylcyclopentenyl)toluene which, on dehydrogenation, will generate diene by-products which are difficult to separate from the desired product and will also inhibit the subsequent oxidation reaction. In the oxidation and esterification steps, different isomers have different reactivity. Thus, para-isomers are more reactive than meta-isomers which are more reactive than ortho-isomers. Also in the dehydrogenation step, the presence of a methyl group in the 2 position on either the cyclohexyl or phenyl ring is a precursor for the formation of fluorene and methyl fluorene. Fluorene is difficult to separate from the dimethylbiphenyl product and causes problems in the oxidation step and also in the plasticizers performance. It is therefore advantageous to minimize the formation of isomers which have a methyl group in the ortho, 2 and benzylic positions.

In a preferred embodiment of the invention, no methyl group is located in the 1-position on the cyclohexyl ring(s) or phenyl ring(s).

In hydroalkylation of toluene, a total of 12 MCHT isomers can be formed (o,y-MCHT, m,y-MCHT, p,y-MCHT, where y=1, 2, 3 or 4). Of these isomers, the x,1 isomers cannot be converted into DMBP by dehydrogenation. Furthermore, the o,y and x,2 isomers form 2,2', 2,3' and 2,4' DMBP upon dehydrogenation and cannot be completely separated from unreacted MCHT by distillation due to overlap in phase change properties. These 2,X' DMBP (sum of 2,2', 2,3' and 2,4' DMBP) isomers can make up>20% of the total DMBP content in the dehydrogenation effluent depending on the catalysts and conditions of the hydroalkylation and dehydrogenation reactions. Therefore, for acceptable process carbon efficiencies, it is useful to minimize 2,X DMBP content and y,1-MCHT isomers. This can be done by applying hydroalkylation catalysts with lower selectivity to the undesired y,1-MCHT isomers and MCHT isomers which form 2,X' DMBP upon dehydrogenation.

Dehydrogenation of Hydroalkylation Product

The major components of the hydroalkylation reaction effluent are (methylcyclohexyl)toluenes and/or (dimethylcyclohexyl)xylenes, unreacted aromatic feed (toluene and/or xylene) and fully saturated single ring by-products (methylcyclohexane and dimethylcyclohexane). The unreacted feed and light by-products can readily be removed from the reaction effluent by, for example, distillation. The unreacted feed can then be recycled to the hydroalkylation reactor, while the saturated by-products can be dehydrogenated to produce additional recyclable feed. The saturated single ring by-products can be dehydrogenated back to the original feed either as a separate reaction step, or in combination with the dehydrogenation of the desired hydroalkylation product to methyl-substituted biphenyls. Further the fully saturated single ring by-products can be recycled back to the hydroalkylation reactor as a liquid to act as a diluent and slow the reactor temperature rise by vaporization.

The remainder of the hydroalkylation reaction effluent, composed mainly of (methylcyclohexyl)toluenes and/or (dimethylcyclohexyl)xylenes, is then dehydrogenated to produce the corresponding methyl-substituted biphenyl compounds. The dehydrogenation is conveniently conducted at a temperature from about 200° C. to about 600° C. and a pressure from about 100 kPa to about 3550 kPa (atmospheric to about 500 psig) in the presence of dehydrogenation catalyst. A suitable dehydrogenation catalyst comprises one or more elements or compounds thereof selected from Group 10 of the Periodic Table of Elements, for example platinum, on a support, such as silica, alumina or carbon nanotubes. In one embodiment, the Group 10 element is present in amount from 0.1 to 5 wt % of the catalyst. In some cases, the dehydrogenation catalyst may also include tin or a tin compound to improve the selectivity to the desired methyl-substituted biphenyl product. In one embodiment, the tin is present in amount from 0.05 to 2.5 wt % of the catalyst.

In a preferred embodiment of the invention, the product of the dehydrogenation step comprises methyl-substituted biphenyl compounds in which the concentration of the 3,3-, 3,4- and 4,4-dimethyl isomers is at least 50 wt %, such as at least 60 wt %, for example at least 70 wt %, based on the total weight of methyl-substituted biphenyl isomers. In addition, the product may contain less than 10 wt %, such as less than 5 wt %, for example less than 3 wt % of methyl biphenyl compounds. Also, the product may contain less than 30 wt %, such as less than 20 wt %, for example less than 10 wt % of biphenyl compounds having a methyl group at one or both 1 positions (quaternary carbon). Likewise, the product may contain less than 10 wt %, such as less than 5 wt %, for example less than 2 wt % of the combined amount of biphenyl compounds having an ortho or para methyl group and a methyl group at a 1 position (quaternary carbon).

In a preferred embodiment of the invention, the reacting step (a) is conducted with toluene, further comprising the steps of: reacting toluene in the presence of $H_2$ and a hydrogenation catalyst to form methyl cyclohexene; reacting said methyl cyclohexene with toluene in the presence of an alkylation catalyst to form dimethyl cyclohexylbenzene; and dehydrogenating said dimethyl cyclohexylbenzene in the presence of a dehydrogenation catalyst to form the alkylated biphenyl, which is preferably dimethyl-biphenyl.

Production of Biphenyl Esters

The methyl-substituted biphenyl compounds produced by the dehydrogenation reaction can readily be converted to ester plasticizers by a process comprising oxidation to produce the corresponding carboxylic acids followed by esterification with an alcohol. The oxidation can be performed by any process known in the art, such as by reacting the methyl-substituted biphenyl compounds with an oxidant, such as oxygen, ozone or air, or any other oxygen source, such as hydrogen peroxide, in the presence of a catalyst at temperatures from 30° C. to 300° C., such as from 60° C. to 200° C. Suitable catalysts comprise Co or Mn or a combination of both metals.

The resulting carboxylic acids can then be esterified to produce biphenyl ester plasticizers by reaction with one or more $C_1$ to $C_{14}$ alcohols, typically $C_4$ to $C_{14}$ alcohols. Suitable esterification conditions are well-known in the art and include, but are not limited to, temperatures of 0-300° C. and the presence or absence of homogeneous or heterogeneous esterification catalysts, such as Lewis or Bronsted acid catalysts. Useful $C_1$ to $C_{14}$ alcohols (alternately $C_4$ to $C_{14}$ alcohols), include OXO-alcohols, by which is meant an organic alcohol, or mixture of organic alcohols, which is prepared by hydroformylating an olefin, followed by hydrogenation to form the alcohols. Typically, the olefin is formed by light olefin oligomerization over heterogeneous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety. Another source of olefins used in the OXO process are through the oligomerization of ethylene, producing mixtures of predominately straight chain alcohols with lesser amounts of lightly branched alcohols.

In a preferred embodiment of the invention, in the production of methylbiphenylester (from toluene feed) the dimethylbiphenyl intermediate is then oxidized to the monoacid and then esterified to make methylbiphenylester. In the case of 3,4' or 4,4' biphenyl dicarboxylic acid production, both methyl groups would be oxidized. Prior to oxidation, the dimethylbiphenyl is separated from methylcyclohexyltoluene that was unreacted in the dehydrogenation process.

In an embodiment of the invention, the di-ester is prepared generally as follows:

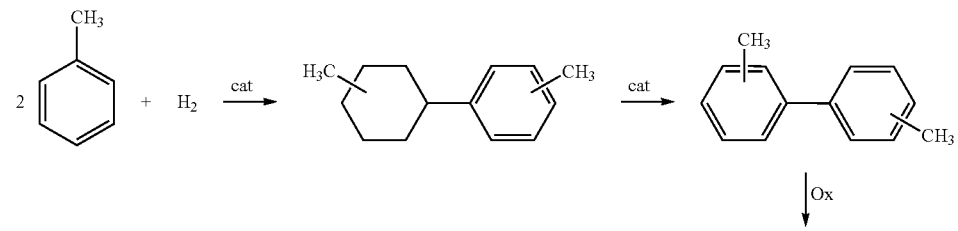

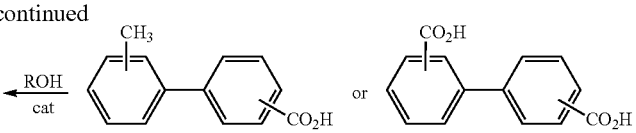

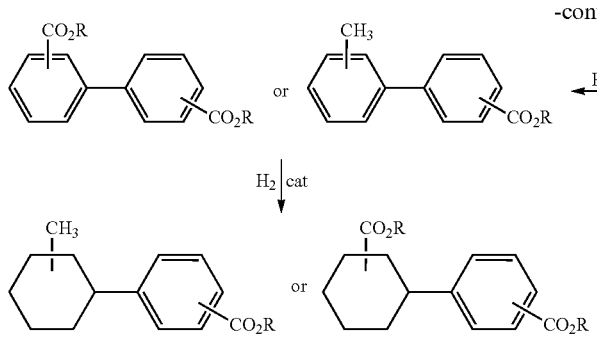

wherein ROH is a branched alcohol, preferably an OXO-alcohol, preferably a typically $C_1$ to $C_{14}$ OXO-alcohol, even more preferably a $C_4$ to $C_{14}$ OXO-alcohol, and R is a $C_1$ to $C_{14}$ hydrocarbyl (preferably a $C_4$ to $C_{14}$ hydrocarbyl), preferably branched. Either monoesters or diesters can be formed, or both, depending on reaction conditions. Likewise, by appropriate control of the oxidation step so as to oxidize only one of the pendant methyl groups, monoester compounds of the following general formula can be formed:

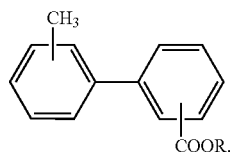

Alternatively, one mole of toluene can be hydrogenated to form methyl cyclohexene, and then the methyl cyclohexene used to alkylate another mole of toluene, followed by dehydrogenation to form dimethyl biphenyl.

In a more preferred embodiment, the resulting alkylated aromatic compound is oxidized to acid/diacid, then esterified with OXO-alcohols, which are mixed linear and branched alcohol isomers, the formation of which is described in more detail below.

"OXO-alcohols" are isomeric mixtures of branched, organic alcohols. "OXO-esters" are compounds having at least one functional ester moiety within its structure derived from esterification of a carboxylic acid portion or moiety of a compound with an OXO-alcohol. OXO-alcohols can be prepared by hydroformylating olefins, followed by hydrogenation to form the alcohols. "Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (OXO) process. The resulting OXO-alcohols consist of multiple isomers of a given chain length due to the various isomeric olefins obtained in the oligomerization process, described below, in tandem with the multiple isomeric possibilities of the hydroformylation step.

Typically, the isomeric olefins are formed by light olefin oligomerization over heterogeneous acid catalysts, such as by propylene and/or butene oligomerization over solid phosphoric acid or zeolite catalysts. The light olefins are readily available from refinery processing operations. The reaction results in mixtures of longer-chain, branched olefins, which are subsequently formed into longer chain, branched alcohols, as described below and in U.S. Pat. No. 6,274,756, incorporated herein by reference in its entirety. Olefins for hydroformylation can also be prepared by dimerization of propylene or butenes through commercial processes such as the IFP Dimersol™ process or the Huls (Evonik) Octol™ process. Branched aldehydes are then produced by hydroformylation of the isomeric olefins. The resulting branched aldehydes can then be recovered from the crude hydroformylation product stream by fractionation to remove unreacted olefins. These branched aldehydes can then be hydrogenated to form alcohols (OXO-alcohols). Single carbon number alcohols can be used in the esterification of the acids described above, or differing carbon numbers can be used to optimize product cost and performance requirements. The "OXO" technology provides cost advantaged alcohols. Other options are considered, such as hydroformylation of $C_4$-olefins to $C_5$-aldehydes, followed by hydrogenation to $C_5$-alcohols, or aldehyde dimerization followed by hydrogenation to $C_{10}$ alcohols.

"Hydrogenating" or "hydrogenation" is addition of hydrogen ($H_2$) to a double-bonded functional site of a molecule, such as in the present case the addition of hydrogen to the aldehyde moieties of a di-aldehyde, to form the corresponding di-alcohol, and saturation of the double bonds in an aromatic ring. Conditions for hydrogenation of an aldehyde are well-known in the art and include, but are not limited to temperatures of 0-300° C., pressures of 1-500 atmospheres, and the presence of homogeneous or heterogeneous hydrogenation catalysts such as, but not limited to Pt/C, Pt/Al$_2$O$_3$ or Pd/Al$_2$O$_3$ and Ni. Useful hydrogenation catalysts include platinum, palladium, ruthenium, nickel, zinc, tin, cobalt, or a combination of these metals, with palladium being particularly advantageous.

Alternatively, the OXO-alcohols can be prepared by aldol condensation of shorter-chain aldehydes to form longer chain aldehydes, as described in U.S. Pat. No. 6,274,756, followed by hydrogenation to form the OXO-alcohols.

"Esterifying" or "esterification" is reaction of a carboxylic acid moiety, such as an anhydride, with an organic alcohol moiety to form an ester linkage. Esterification conditions are well-known in the art and include, but are not limited to, temperatures of 0-300° C., and the presence or absence of homogeneous or heterogeneous esterification catalysts such as Lewis or Brønsted acid catalysts.

In a preferred embodiment of the invention, after reacting the acid group(s) with an OXO-alcohol under esterification conditions, the reaction product is contacted with a basic solution such as saturated sodium bicarbonate or a caustic soda wash.

In a preferred embodiment of the invention, the crude ester is further stripped to remove excess alcohol and the stripped plasticizer is treated with activated carbon to improve the liquid volume resistivity of the plasticizer.

As discussed above, the resulting OXO-alcohols can be used individually or together in alcohol mixtures having different chain lengths, or in isomeric mixtures of the same carbon chain length to make mixed esters for use as plasticizers. This mixing of carbon numbers and/or levels of branching can be advantageous to achieve the desired compatibility with PVC for the respective core alcohol or acid used for the polar moiety end of the plasticizer, and to meet other plasticizer performance properties. The preferred OXO-alcohols are those having from 5 to 13 carbons, preferably $C_5$ to $C_{11}$ alcohols, and preferably $C_6$ to $C_{10}$ alcohols. In a preferred embodiment, the OXO-alcohol is selected from C1, C2, C3, C4, C5, C6, C7, C8, C9, C10, C11, C12, C13 and C14 OXO-alcohols.

In an embodiment, the preferred OXO-alcohols are those which have an average branching of from 0.2 to 5.0 branches per molecule, and from 0.35 to 5.0 methyl branches per molecule, or even from 1.3 to 5.0 methyl branches per molecule. In a more preferred embodiment, the alcohols have from 0.05 to 0.4 branches per residue at the alcoholic beta carbon.

Typical branching characteristics of OXO-alcohols are provided in Table 1, below.

TABLE 1

$^{13}$C NMR Branching Characteristics of Typical OXO-Alcohols.

| OXO-Alcohol | Avg. Carbon No. | % of α-Carbons w/ Branches[a] | β-Branches per Molecule[b] | Total Methyls per Molecule[c] | Pendant Methyls per Molecule[d] | Pendant Ethyls per Molecule |
|---|---|---|---|---|---|---|
| $C_4$[e] | 4.0 | 0 | 0.35 | 1.35 | 0.35 | 0 |
| $C_5$[f] | 5.0 | 0 | 0.30 | 1.35 | 0.35 | 0 |
| $C_6$ | — | — | — | — | — | — |
| $C_7$ | 7.2 | 0 | 0.13 | 2.2 | — | 0.04 |
| $C_8$ | 8.0 | 0 | 0.08 | 2.6 | — | — |
| $C_9$ | 9.3 | 0 | 0.09 | 3.1 | — | — |
| $C_{10}$ | 10.1 | 0 | 0.08 | 3.1 | — | — |
| $C_{12}$ | 11.8 | 0 | 0.09 | 3.9 | — | — |
| $C_{13}$ | 12.7 | 0 | 0.09 | 3.9 | — | — |

— Data not available.
[a] —COH carbon.
[b] Branches at the —CCH$_2$OH carbon.
[c] This value counts all methyl groups, including $C_1$ branches, chain end methyls, and methyl endgroups on $C_2$+ branches.
[d] $C_1$ branches only.
[e] Calculated values based on an assumed molar isomeric distribution of 65% n-butanol and 35% isobutanol (2-methylpentanol).
[f] Calculated values based on an assumed molar isomeric distribution of 65% n-pentanol, 30% 2-methylbutanol, and 5% 3-methylbutanol.

In a preferred embodiment of the invention, the alcohol (such as an OXO-alcohol) has 2.0 to 3.5 methyl branches per molecule, typically 2.1 to 3.3.

In general, for every polymer to be plasticized, a plasticizer is required with a good balance of polarity or solubility, volatility and viscosity to have acceptable plasticizer compatibility with the resin. In particular, if the 20° C. kinematic viscosity is higher than 250 mm$^2$/sec as measured by the appropriate ASTM test, or alternately if the 20° C. cone-and-plate viscosity is higher than 250 cP, this will affect the plasticizer processability during formulation, and can require heating the plasticizer to ensure good transfer during storage and mixing of the polymer and the plasticizer. Volatility is also an important factor which affects the ageing or durability of the plasticized polymer. Highly volatile plasticizers will diffuse and evaporate from the plastic resin matrix, thus losing mechanical strength in applications requiring long term stability/flexibility. Relative plasticizer loss from a resin matrix due to plasticizer volatility can be roughly predicted by neat plasticizer weight loss at 220° C. using Thermogravimetric Analysis.

We have found that when $C_4$ to $C_{14}$ OXO-alcohols are used as reactants for the esterification reactions described above, the resulting OXO-esters are in the form of relatively high-boiling liquids (having low volatility), which are readily incorporated into polymer formulations as plasticizers.

Any of the esters can have R groups which contain mixed alkyl isomer residues of $C_4$ to $C_{14}$ OXO-alcohols, can be used as plasticizers for polymers, such as vinyl chloride resins, polyesters, polyurethanes, silylated polymers, polysulfides, acrylics, ethylene-vinyl acetate copolymer, rubbers, poly(meth)acrylics and combinations thereof, preferably polyvinylchloride. In particular, one could use mixed alcohols isomers to form mixed esters with mixed alkyl isomers residue of $C_4$ to $C_{14}$ OXO-alcohols to obtain the mixed alkyl isomer residues.

Dicarboxylic Esters

It has been determined that compounds produced herein of the general formula:

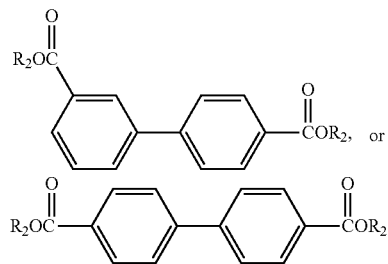

wherein $R_2$ is a $C_1$ to $C_{14}$ hydrocarbyl (preferably $C_4$ to $C_{14}$ hydrocarbyl), preferably the residue of a $C_1$ to $C_{14}$ OXO-alcohol (preferably a $C_4$ to $C_{14}$ OXO-alcohol), are particularly useful as plasticizers. In a preferred embodiment of the invention, both ortho positions of both phenyl rings are hydrogen. In a preferred embodiment of the invention, both meta positions of both phenyl rings are hydrogen. In a preferred embodiment of the invention, both ortho positions and both meta positions of both phenyl rings are hydrogen.

The biphenyl ester plasticizers of the present application find use in a number of different polymers, such as vinyl chloride resins, polyesters, polyurethanes, ethylene-vinyl acetate copolymers, rubbers, poly(meth)acrylics and mixtures thereof.

In a preferred embodiment, this invention relates to polymer composition comprising a thermoplastic polymer and at least one plasticizer described herein, preferably where the thermoplastic polymer is selected from the group consisting of vinyl chloride resins, polyesters, polyurethanes, ethylene-vinyl acetate copolymer, rubbers, poly(meth)acrylics and combinations thereof, alternately the polymer is selected from the group consisting of polyvinyl chloride (PVC), polyvinylidene chloride, a copolymer of polyvinyl chloride and polyvinylidene chloride, and polyalkyl methacrylate (PAMA), preferably the polymer is a copolymer of vinyl chloride with at least one monomer selected from the group consisting of vinylidene chloride, vinyl acetate, vinyl propionate, vinyl butyrate, vinyl benzoate, methyl acrylate, ethyl acrylate, and butyl acrylate.

In any embodiment of the invention, in the polymer composition comprising a thermoplastic polymer and at least one plasticizer, the amount of plasticizer is from 5 to 90 wt %, based upon the weight of the polymer and plasticizer, preferably from 10 to 100 wt %, even more preferably in the range from 15 to 90 wt %, preferably in the range from 20 to 80 wt %.

The polymer composition comprising a thermoplastic polymer and at least one plasticizer described herein may optionally contain further additional plasticizers other than those produced herein, such as: dialkyl(ortho)phthalate, preferably having 4 to 13 carbon atoms in the alkyl chain; trialkyl trimellitates, preferably having 4 to 10 carbon atoms in the side chain; dialkyl adipates, having 4 to 13 carbon atoms; dialkyl sebacates preferably having 4 to 13 carbon atoms; dialkyl azelates preferably having 4 to 13 carbon atoms; preferably dialkyl terephthalates each preferably having 4 to 8 carbon atoms and more particularly 4 to 7 carbon atoms in the side chain; alkyl 1,2-cyclohexanedicarboxylates, alkyl 1,3-cyclohexanedicarboxylates and alkyl 1,4-cyclohexanedicarboxylates, and preferably here alkyl 1,2-cyclohexanedicarboxylates each preferably having 4 to 13 carbon atoms in the side chain; dibenzoic esters of glycols; alkylsulfonic esters of phenol with preferably one alkyl radical containing 8 to 22 carbon atoms; polymeric plasticizers (based on polyester in particular), glyceryl esters, acetylated glycerol esters, epoxy estolide fatty acid alkyl esters, citric triesters having a free or carboxylated OH group and for example alkyl radicals of 4 to 9 carbon atoms, alkylpyrrolidone derivatives having alkyl radicals of 4 to 18 carbon atoms and also alkyl benzoates, preferably having 7 to 13 carbon atoms in the alkyl chain. In all instances, the alkyl radicals can be linear or branched and the same or different.

The polymer composition comprising a thermoplastic polymer and at least one plasticizer described herein prepared according to the present invention may further contain additives to optimize the chemical, mechanical or processing properties, said additives being more particularly selected from the group consisting of fillers, such as calcium carbonate, titanium dioxide or silica, pigments, thermal stabilizers, antioxidants, UV stabilizers, lubricating or slip agents, flame retardants, antistatic agents, biocides, impact modifiers, blowing agents, (polymeric) processing aids, viscosity depressants or regulators such as thickener and thinners, antifogging agents, optical brighteners, etc.

Thermal stabilizers useful herein include all customary polymer stabilizers, especially PVC stabilizers in solid or liquid form, examples are those based on Ca/Zn, Ba/Zn, Pb, Sn or on organic compounds (OBS), and also acid-binding phyllosilicates such as hydrotalcite. The mixtures to be used according to the present invention may have a thermal stabilizer content of 0.5 to 10, preferably 0.8 to 5 and more preferably 1.0 to 4 wt %, based upon the weight of the polymer composition.

It is likewise possible to use costabilizers with plasticizing effect in the polymer composition comprising a thermoplastic polymer and at least one plasticizer as described herein, in particular epoxidized vegetable oils, such as epoxidized linseed oil or epoxidized soya oil.

Antioxidants are also useful in the polymer composition comprising a thermoplastic polymer and at least one plasticizer described herein and can include sterically hindered amines—known as HALS stabilizers, sterically hindered phenols, such as Topanol™ CA, phosphites, UV absorbers, e.g., hydroxybenzophenones, hydroxyphenylbenzotriazoles and/or aromatic amines. Suitable antioxidants for use in the compositions of the present invention are also described for example in "Handbook of Vinyl Formulating" (editor: R. F. Grossman; J. Wiley & Sons; New Jersey, US, 2008). The level of antioxidants in the mixtures of the present invention is typically not more than 10 pph, preferably not more than 8 pph, more preferably not more than 6 pph and even more preferably between 0.01 and 5 pph (pph=parts per hundred parts of polymer).

Organic and inorganic pigments can be also used in the polymer composition comprising a thermoplastic polymer and at least one plasticizer as described herein. The level of pigments in the compositions to be used according to the present invention is typically not more than 10 pph, preferably in the range from 0.01 to 5 pph and more preferably in the range from 0.1 to 3 pph. Examples of useful inorganic pigments are $TiO_2$, CdS, $CoO/Al_2O_3$, $Cr_2O_3$. Examples of useful organic pigments are, for example, azo dyes, phthalocyanine pigments, dioxazine pigments and also aniline pigments.

The polymer composition comprising a thermoplastic polymer and at least one plasticizer described herein may contain one or more filler, including mineral and/or synthetic and/or natural, organic and/or inorganic materials, for example, calcium oxide, magnesium oxide, calcium carbonate, barium sulphate, silicon dioxide, phyllosilicate, carbon black, bitumen, wood (e.g. pulverized, as pellets, micropellets, fibers, etc.), paper, natural and/or synthetic fibers, glass, etc.

The compositions described herein can be produced in various ways. In general, however, the composition is produced by intensively mixing all components in a suitable mixing container at elevated temperatures. The plastic pellet or powder (typically suspension PVC, microsuspension PVC or emulsion PVC) is typically mixed mechanically, for example in fluid mixers, turbomixers, trough mixers or belt screw mixers, with the plasticizer and the other components at temperatures in the range from 60° C. to 140° C., preferably in the range from 80° C. to 100° C. The components may be added simultaneously or, preferably, in succession (see also E. J. Wickson "Handbook of PVC Formulating", John Wiley and Sons, 1993, pp. 747 ff). The blend of PVC, plasticizer and other additives as described above (e.g. the PVC compound or the PVC paste) is subsequently sent to the appropriate thermoplastic moulding processes for producing the finished or semi-finished article, optionally a pelletizing step is interposed.

The blends (e.g. the PVC compound or the PVC paste) are particularly useful for production of garden hoses, pipes, and medical tubing, floor coverings, flooring tiles, films, sheeting, roofing, or roofing webs, pool liners, building protection foils, upholstery, and cable sheathing and wire insulation, particularly wire and cable coating, coated textiles and wall coverings.

The plasticizers of the invention are useful across the range of plasticized polyvinyl chloride materials. The plasticizers of the invention are useful in the production of semi-rigid polyvinyl chloride compositions which typically contain from 10 to 40 pph, preferably 15 to 35 pph, more preferably 20 to 30 pph of plasticizer (pph=parts per hundred parts PVC); flexible polyvinyl chloride compositions which typically contain from 40 to 60 pph, preferably 44 to 56 pph, more preferably from 48 to 52 pph plasticizer; and highly flexible compositions which typically contain from 70 to 110 pph, preferably 80 to 100 pph, more preferably 90 to 100 pph of plasticizer.

One widespread use of polyvinyl chloride is as a plastisol. A plastisol is a fluid or a paste consisting of a mixture of polyvinyl chloride and a plasticizer optionally containing various additives, such as those described above. A plastisol is used to produce layers of polyvinyl chloride which are then fused to produce coherent articles of flexible polyvinyl chloride. Plastisols are useful in the production of flooring, tents, tarpaulins, coated fabrics such as automobile upholstery, in car underbody coatings, in mouldings and other consumer products. Plastisols are also used in footwear, fabric coating, toys, flooring products and wallpaper. Plastisols typically contain 40 to 200 pph, more typically 50 to 150 pph, more typically 70 to 120 pph, more typically 90 to 110 pph of plasticizer.

In a preferred embodiment of the invention, one or more (such as two or three) plasticizers produced herein are combined with a polymer such as PVC to form a PVC compound (typically made from suspension PVC) or a PVC paste (typically made from an emulsion PVC). A particularly useful PVC in the PVC compound or paste is one having a K value above 70. Particularly preferred PVC compounds or paste comprise: 20 to 100 pph plasticizer(s) and/or 0.5 to 15 pph stabilizer(s), and/or 1 to 30 pph, preferably 15 to 30 pph, filler(s), even more preferably the filler is calcium carbonate and the stabilizer is a calcium/zinc stabilizer. The above combination is useful in wire and cable coatings, particularly automobile wire and cable coating and or building wire insulation.

In general, a particularly good (i.e. low) glass transition temperature is achievable for the polymer compositions of the present invention by using plasticizer which itself has a low glass transition temperature and/or by using a high plasticizer content. Polymer compositions of the present invention may have glass transition temperatures in the range from −70° C. to +10° C., preferably in the range from −60° C. to −5° C., more preferably in the range from −50° C. to −20° C. and most preferably in the range from −45° C. to −30° C. Tg of the polymer composition is determined using DMTA and DSC, as described below. (In the event of conflict between the DMTA and DSC results, DMTA shall be used). Tg of the neat plasticizer is determined using DSC as described below.

This invention also relates to:
1. A process for producing (methylcyclohexyl)toluene, the process comprising:
  (a) contacting a feed comprising toluene, xylene or mixtures thereof with hydrogen in the presence of a hydroalkylation catalyst under conditions effective to produce a hydroalkylation reaction product comprising (methylcyclohexyl)toluene, wherein the hydroalkylation catalyst comprises: 1) binder present at 40 wt % or less, 2) a hydrogenation component present at 0.2 wt % or less, and 3) an acidic component comprising a molecular sieve having a twelve membered (or larger) ring pore opening, channel or pocket and a largest pore dimension of 6.0 angstroms or more present at 60 wt % or more, (each based upon weight of final catalyst composition).
2. The process of paragraph 1, further comprising producing methyl-substituted biphenyl compounds, the process further comprising:
  (b) dehydrogenating at least part of the hydroalkylation reaction product in the presence of a dehydrogenation catalyst under conditions effective to produce a dehydrogenation reaction product comprising a mixture of methyl-substituted biphenyl compounds.
3. The process of paragraph 2, further comprising producing biphenyl carboxylic acids, the process further comprising:
  (c) contacting at least part of the dehydrogenation reaction product with an oxidizing gas under conditions effective to convert at least part of the methyl-substituted biphenyl compounds to biphenyl carboxylic acids.
4. The process of paragraph 3, further comprising producing biphenyl esters, the process further comprising:
  (d) reacting the biphenyl carboxylic acids with one or more $C_1$ to $C_{14}$ alcohols (such as one or more OXO-alcohols, preferably branched, preferably having an average branching of from 0.2 to 5.0 branches per molecule, and optionally 0.35 to 5.0 methyl branches per molecule) under conditions effective to produce biphenyl esters.
5. The process of any of paragraphs 1 to 4, wherein the molecular sieve is selected from the group consisting of ZSM-12, zeolite Beta, faujasite, mordenite, and mixtures thereof.
6. The process of any of paragraphs 1 to 4, wherein the molecular sieve is selected from the group consisting of zeolite Y, Ultrastable Y (USY), Dealuminated Y (Deal Y), mordenite and mixtures thereof.
7. The process of any of paragraphs 1 to 6, wherein the molecular sieve does not comprise a molecular sieve of the MCM-22 family.
8. The process of any of paragraphs 1 to 7, wherein the hydrogenation component of the hydroalkylation catalyst is selected from the group consisting of palladium, ruthenium, nickel, zinc, tin, cobalt and compounds and mixtures thereof.
9. The process of any of paragraphs 1 to 8, wherein the binder component of the hydroalkylation catalyst is selected from pseudoboehmite alumina, alumina, silica, titania and mixtures thereof.
10. The process of any of paragraphs 1 to 9, wherein the molar ratio of hydrogen to feed (e.g. aromatic feed) supplied to the contacting (a) is from about 0.15:1 to about 15:1.
11. The process of any of paragraphs 1 to 10, wherein the hydroalkylation reaction product comprises less than 5 wt % of compounds having a methyl group at the 1 position.
12. The process of any of paragraphs 1 to 11, wherein the feed further comprises benzene and/or at least one alkylbenzene different from toluene and xylene.
13. The process of any of paragraphs 1 to 12, wherein the dehydrogenation catalyst comprises an element or compound thereof selected from Group 10 of the Periodic Table of Elements.
14. The process of any of paragraphs 2 to 13, wherein the dehydrogenation conditions in (b) include a temperature from about 200° C. to about 600° C. and a pressure from about 100 kPa to about 3550 kPa (atmospheric to about 500 psig).
15. The process of any of paragraphs 1 to 14, wherein the conditions in the contacting (a) include a temperature from about 100° C. to about 400° C. and a pressure from about 100 to about 7,000 kPa.
16. The process of any of paragraphs 1 to 11, 13, 14 or 15 wherein the feed consists essentially of toluene.

EXPERIMENTAL

The following examples are meant to illustrate the present disclosure and inventive processes, and provide where appropriate, a comparison with other methods, including the products produced thereby. Numerous modifications and variations are possible and it is to be understood that within the scope of the appended claims, the disclosure can be practiced otherwise than as specifically described herein.

EXAMPLES

A general preparation procedure for the Pd-based catalysts considered here is given below. For the example of a preparation of a 0.3 wt % Pd/80 wt % zeolite/20 wt % binder catalyst, 80 parts zeolite crystals are combined with 20 parts pseudoboehmite alumina, on a calcined dry weight basis. The beta and pseudoboehmite are mixed in a muller for about 15 to 60 minutes. Sufficient water and 1.0% nitric acid is added during the mixing process to produce an extrudable paste. The extrudable paste is formed into a ¹⁄₂₀ inch quadrulobe extrudate using an extruder. After extrusion, the ¹⁄₂₀th inch quadrulobe extrudate is dried at a temperature ranging from 250° F. to 325° F. (120° C. to 163° C.). After drying, the dried extrudate is heated to 1000° F. (538° C.) under flowing nitrogen and then calcined in air at a temperature of 1000° F. (538° C.). Afterwards, the calcined extrudate is cooled to room temperature. The 80% zeolite, 20% $Al_2O_3$ extrudate is impregnated using incipient wetness impregnation with a Palladium (II) chloride solution (target: 0.30 wt % Pd) and then dried overnight at 121° C. The dried catalyst was calcined in air at the following conditions: 5 volumes air per volume catalyst per minute, ramp from ambient to 538° C. at 1° C./min and hold for 3 hours.

The catalysts in this example were activated in-situ by heating up to 300° C. at 5° C./min and holding at 300° C. for 2 hours before cooling down to the desired hydroalkylation reaction temperature. Where indicated, Pd dispersion was measured by oxygen chemisorption after reduction.

All toluene hydroalkylation tests described in the examples below were carried out in a 7 mm diameter×150 mm isothermal reactor, equipped with a 1.6 mm internal thermowell for temperature monitoring. About 2 grams of catalyst, sized to 0.4-0.6 mm particles, were diluted with $SiC_x$ and loaded into the reactor tube. Normal testing conditions were at a weight-hourly-space-velocity of 2 $h^{-1}$ (on a toluene basis) at 140-160° C. and 11-20 barg. The $H_2$ and toluene feed were mixed using a high efficiency static mixer and the $H_2$:toluene molar ratio was maintained at either 1 or 2.

Liquid samples were collected from the reactor effluent at process pressure. Analysis of the liquid samples was performed on an Agilent 7890 GC equipped with an autosampler and 150 vial sample tray. The following GC method was used:

Inlet Temp: 230° C.,
Detector Temp: 220° C. (Col+make up=constant),
Temperature Program: Initial 140° C. hold for 20 min, ramp @ 2° C./min to 180° C., hold 12 min, ramp @ 20° C./min to 220° C. and hold 6 min,
Column Flow: 2.5 ml/min; split mode, split ratio 200:1,
Injector: Auto sampler (1 µl), Column Parameters:
Two columns joined to make 120 Meters (coupled with Agilent ultimate union, deactivated.
Column # Front end: Supelco β-Dex 120; 60 m×0.25 mm×0.25 µm film joined to Column #2 back end:γ-Dex 325: 60 m×0.25 mm×0.25 µm film.

Figure 2:
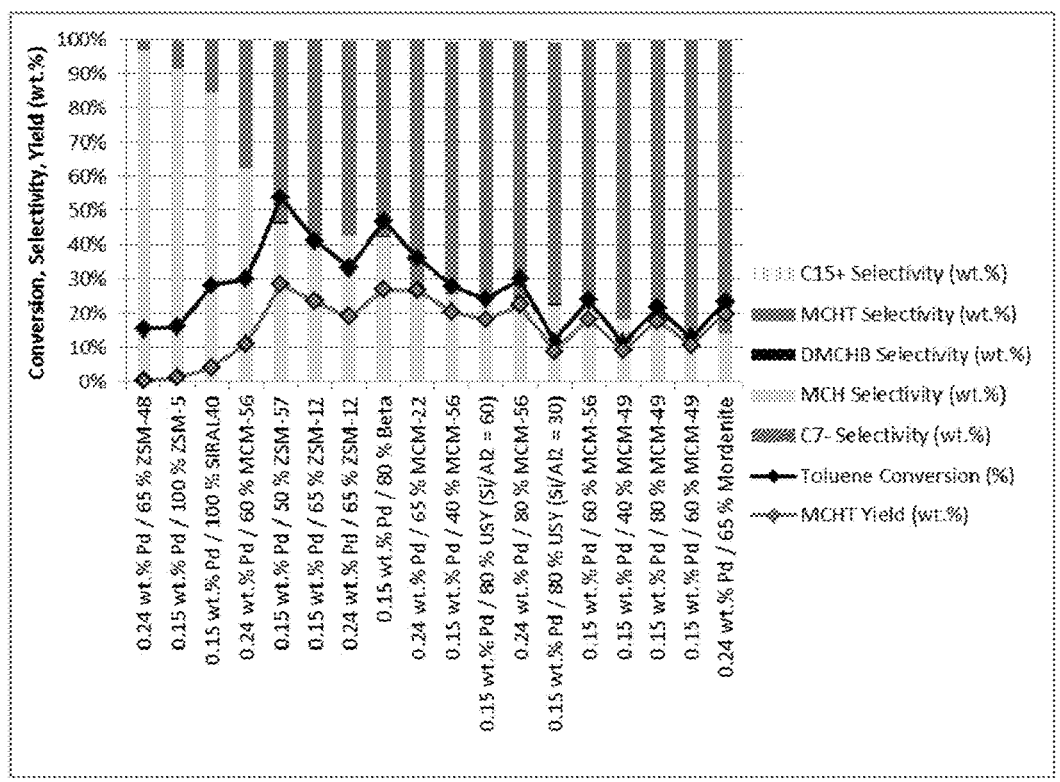
FIG. 2 is a graph of conversion and selectivity for the catalysts containing various zeolite or amorphous solid acid functions at various concentrations. Conditions: WHSV=2 $h^{-1}$, 140° C., 11 barg, $H_2$:Toluene=1 and 90-140 h time-on-stream.
Figure 3:
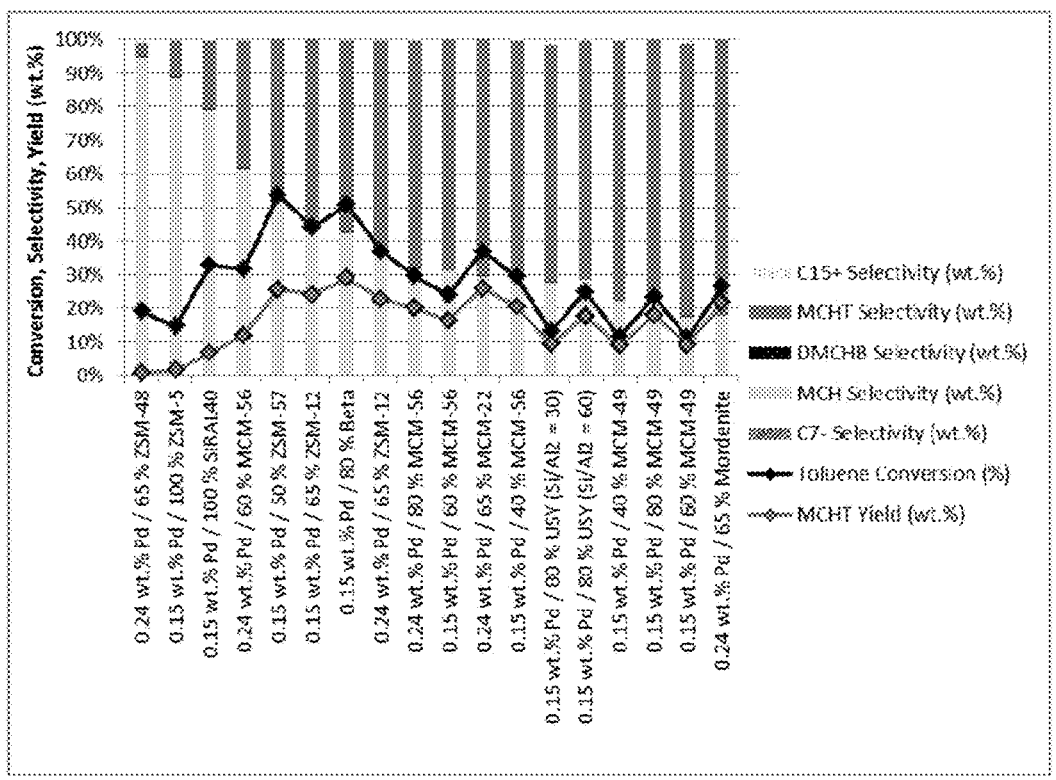
FIG. 3 is a graph of conversion and selectivity for the catalysts containing various zeolite or amorphous solid acid functions at various concentrations. Conditions: WHSV=2 $h^{-1}$, 140° C., 11 barg, $H_2$:Toluene=2 and 60-90 h time-on-stream.

Example 1: Improved MCHT Yield and Isomer Distribution by Varying the Zeolite Function in Hydroalkylation Catalysts Table 2 and Table 3 show the conversion, selectivity and MCHT isomer distribution for the considered catalysts at WHSV=2 $h^{-1}$, 140° C. a $H_2$:Toluene molar ratio of 1 and 2, respectively. FIG. 2 and FIG. 3 present the toluene conversion and primary product selectivity and MCHT isomer distribution for the materials at $H_2$:Toluene molar ratio of 1 and 2, respectively.

FIG. 2 illustrates that in terms of selectivity to MCHT at comparable conversion, the order is Mordenite>MCM-49>MCM-56=USY=MCM-22>Beta>ZSM-12>ZSM-57>SIRAL40>ZSM-5>ZSM-48. SIRAL40 is a commercial amorphous aluminosilica (Siralox® 40). In general, 12 MR (MR=membered ring) zeolites show better selectivity performance over 10 MR zeolites and amorphous materials. ZSM-5 and ZSM-48 both produced a significant amount of light products (C7−).

The Beta, ZSM-12 and ZSM-57 materials showed superior toluene conversion at similar conditions and Pd content.

FIG. 3 shows the catalyst performance in hydroalkylation for a $H_2$:Toluene molar ratio of 2. Overall, higher toluene conversion and lower selectivity to MCHT are observed at these conditions. The general selectivity trend for the materials under study, however, remained unchanged.

Figure 4:
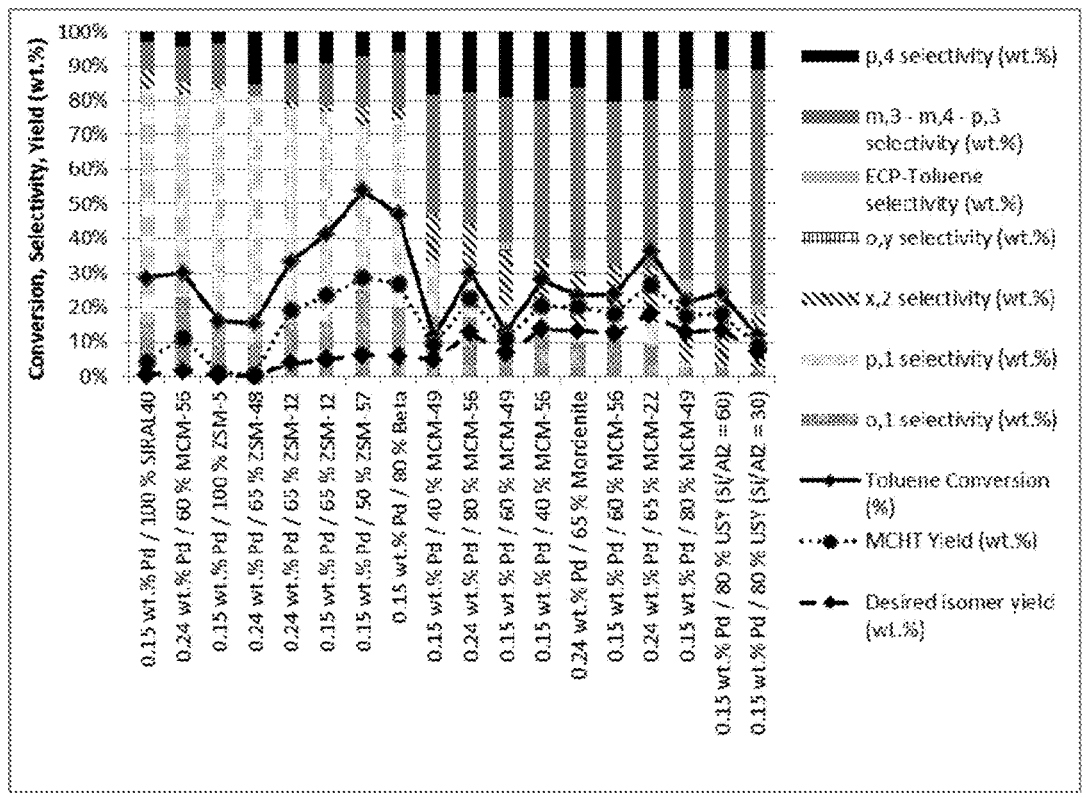
FIG. 4 is a graph of toluene conversion, MCHT yield, desired isomer yield and isomer selectivity within the MCHT fraction (bars) of the product for the catalysts containing various zeolite or amorphous solid acid functions at various concentrations at $H_2$:Toluene=1. Conditions: WHSV=2 $h^{-1}$, 140° C., 11 barg, $H_2$:Toluene=1 and 90-140 h time-on-stream. The x, y nomenclature in the figure refer to x, y-MCHT where x=o, m, p and y=1, 2, 3, 4.
Figure 5:
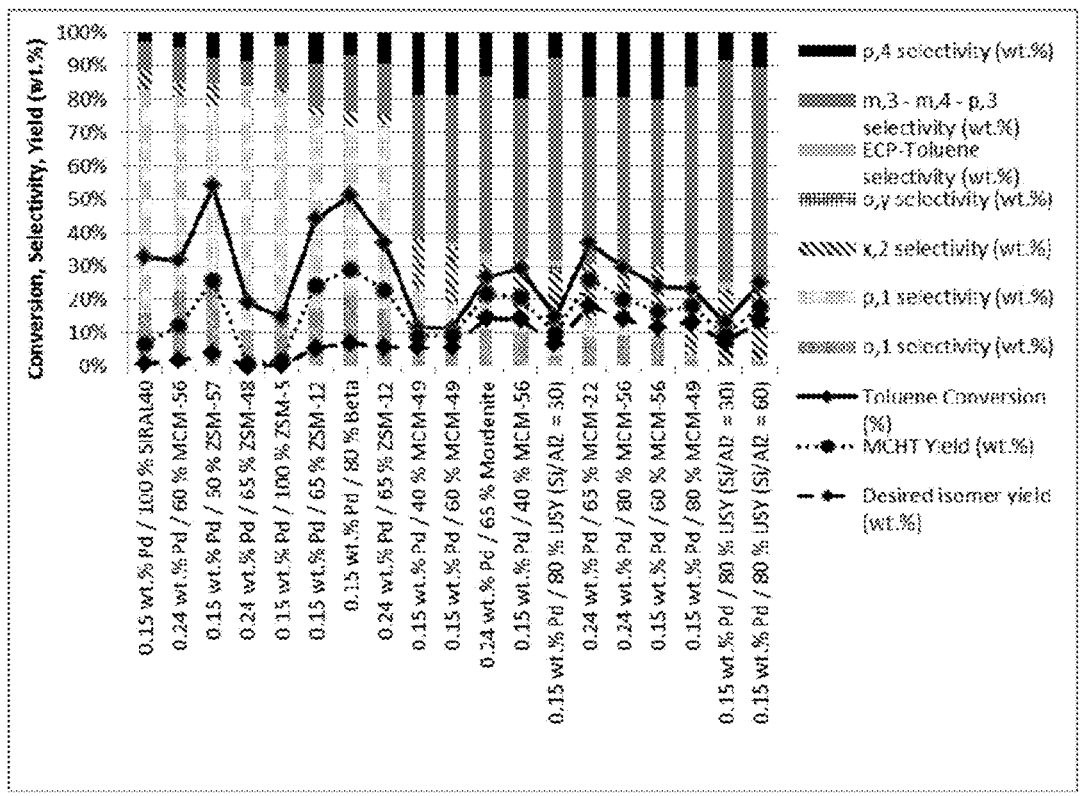
FIG. 5 is a graph of toluene conversion, MCHT yield, desired isomer yield and isomer selectivity within the MCHT fraction (bars) of the product for the catalysts containing various zeolite or amorphous solid acid functions at various concentrations at $H_2$:Toluene=2. Conditions: WHSV=2 $h^{-1}$ 140° C., 11 barg, $H_2$:Toluene=2 and 60-90 h time-on-stream. The x, y nomenclature in the figure refer to x, y-MCHT where x=o, m, p and y=1, 2, 3, 4.

FIG. 4 and FIG. 5 show the MCHT yield and isomer distribution of the produced MCHT species at a $H_2$:Toluene ratio of 1 and 2, respectively. The selectivity to desired isomers (m,3-MCHT, m,4-MCHT, p,3-MCHT, p,4-MCHT) for the different zeolite materials decreases in the order USY>MCM-49=MCM-56=Mordenite=MCM-22>Beta=ZSM-57=ZSM-12>ZSM-48>ZSM-5>>SIRAL40. At >75% desired MCHT isomer selectivity, the 12 membered ring USY based materials clearly showed superior performance over the other materials, albeit at lower overall MCHT yield. The other 12 MR Mordenite and MWW based materials showed overall favorably isomer selectivity over 10 MR and amorphous acid materials, while Beta and ZSM-12 (other 12 MR based materials) showed relatively poor performance.

TABLE 2

Catalytic performance for the materials under study at H2:Toluene = ~1. Performance is compared after 90-140 h on-stream.

| Catalyst | | | Conditions | | | | Conversion and selectivity | | | | | |
|---|---|---|---|---|---|---|---|---|---|---|---|---|
| Pd Loading | Zeolite/ Amorphous Acid | Zeolite/ Acid content | T (° C.) | P (bar) | H2:Toluene (mol:mol) | WHSV ($h^{-1}$) | Toluene Conversion (%) | C7− (wt. %) | MCH (wt. %) | DMCHB (wt. %) | MCHT (wt. %) | C15+ (wt. %) |
| 0.15% | Beta | 80% | 141 | 11.1 | 1.0 | 2.0 | 46.9% | 0.7% | 41.5% | 0.2% | 57.5% | 0.1% |
| 0.24% | MCM-22 | 65% | 140 | 11.5 | 1.5 | 1.5 | 36.2% | 0.1% | 26.4% | 0.2% | 73.3% | 0.0% |

TABLE 2-continued

Catalytic performance for the materials under study at H2:Toluene = ~1. Performance is compared after 90-140 h on-stream.

| Pd Loading | Zeolite/Amorphous Acid | Zeolite/Acid content | T (°C) | P (bar) | H2:Toluene (mol:mol) | WHSV (h⁻¹) | | | | | | |
|---|---|---|---|---|---|---|---|---|---|---|---|---|
| 0.15% | MCM-49 | 40% | 140 | 10.6 | 1.0 | 2.0 | 11.4% | 0.0% | 18.1% | 0.2% | 81.0% | 0.7% |
| 0.15% | MCM-49 | 60% | 140 | 10.7 | 1.0 | 2.0 | 12.9% | 0.1% | 15.1% | 0.2% | 84.4% | 0.1% |
| 0.15% | MCM-49 | 80% | 140 | 11.1 | 1.0 | 1.9 | 21.6% | 0.1% | 18.1% | 0.1% | 81.6% | 0.1% |
| 0.15% | MCM-56 | 40% | 141 | 11.5 | 1.0 | 2.0 | 28.0% | 0.1% | 25.7% | 0.1% | 73.5% | 0.7% |
| 0.15% | MCM-56 | 60% | 140 | 11.4 | 1.5 | 1.4 | 23.9% | 0.1% | 23.1% | 0.1% | 76.7% | 0.1% |
| 0.24% | MCM-56 | 60% | 140 | 10.7 | 1.1 | 1.9 | 30.1% | 0.2% | 62.2% | 0.1% | 37.3% | 0.1% |
| 0.24% | MCM-56 | 80% | 140 | 11.2 | 1.2 | 1.8 | 30.1% | 0.0% | 24.5% | 0.1% | 75.2% | 0.2% |
| 0.24% | Mordenite | 65% | 139 | 10.5 | 1.1 | 3.4 | 23.3% | 0.2% | 13.9% | 0.1% | 85.7% | 0.1% |
| 0.15% | SIRAL-40 | 100% | 141 | 10.6 | 1.0 | 2.0 | 28.4% | 0.4% | 84.4% | 0.0% | 15.2% | 0.0% |
| 0.15% | USY (Si/Al2 = 30) | 80% | 139 | 10.4 | 1.0 | 2.0 | 11.8% | 0.7% | 21.9% | 0.2% | 76.2% | 1.1% |
| 0.15% | USY Si/Al2 = 60) | 80% | 140 | 11.2 | 1.4 | 1.6 | 24.2% | 0.2% | 24.2% | 0.1% | 75.1% | 0.4% |
| 0.15% | ZSM-12 | 65% | 140 | 10.7 | 1.4 | 1.5 | 41.2% | 0.6% | 42.3% | 0.2% | 56.9% | 0.0% |
| 0.24% | ZSM-12 | 65% | 139 | 10.3 | 1.0 | 2.0 | 33.3% | 0.7% | 41.7% | 0.0% | 57.3% | 0.2% |
| 0.24% | ZSM-48 | 65% | 140 | 11.1 | 1.0 | 3.6 | 15.5% | 2.2% | 94.6% | 0.1% | 2.9% | 0.2% |
| 0.15% | ZSM-5 | 100% | 139 | 11.2 | 1.4 | 1.5 | 16.0% | 3.0% | 88.5% | 0.1% | 8.1% | 0.3% |
| 0.15% | ZSM-57 | 50% | 143 | 10.6 | 1.4 | 1.5 | 53.8% | 0.3% | 46.0% | 0.4% | 53.1% | 0.2% |

| Catalyst | | | Conditions | | | | Conversion and selectivity | MCHT isomer distribution | | | |
|---|---|---|---|---|---|---|---|---|---|---|---|
| | | | | | | | | | | m,3-p,3- | |
| Pd Loading | Zeolite/Amorphous Acid | Zeolite/Acid content | T (°C) | P (bar) | H2:Toluene (mol:mol) | WHSV (h⁻¹) | MCHT Yield (wt. %) | o,1-MCHT (wt. %) | p,1-MCHT (wt. %) | m,4-p,4 isomers (wt. %) | Other isomers (wt. %) |
| 0.15% | Beta | 80% | 141 | 11.1 | 1.0 | 2.0 | 27.0% | 20.0% | 54.2% | 21.9% | 3.9% |
| 0.24% | MCM-22 | 65% | 140 | 11.5 | 1.5 | 1.5 | 26.6% | 9.6% | 5.8% | 68.6% | 16.0% |
| 0.15% | MCM-49 | 40% | 140 | 10.6 | 1.0 | 2.0 | 9.2% | 17.4% | 15.9% | 53.2% | 13.5% |
| 0.15% | MCM-49 | 60% | 140 | 10.7 | 1.0 | 2.0 | 10.9% | 12.6% | 7.8% | 61.5% | 18.1% |
| 0.15% | MCM-49 | 80% | 140 | 11.1 | 1.0 | 1.9 | 17.7% | 2.6% | 1.3% | 72.2% | 23.9% |
| 0.15% | MCM-56 | 40% | 141 | 11.5 | 1.0 | 2.0 | 20.6% | 11.6% | 6.9% | 66.2% | 15.3% |
| 0.15% | MCM-56 | 60% | 140 | 11.4 | 1.5 | 1.4 | 18.4% | 10.7% | 5.9% | 67.9% | 15.5% |
| 0.24% | MCM-56 | 60% | 140 | 10.7 | 1.1 | 1.9 | 11.2% | 22.7% | 58.9% | 14.5% | 3.9% |
| 0.24% | MCM-56 | 80% | 140 | 11.2 | 1.2 | 1.8 | 22.6% | 17.0% | 12.8% | 56.0% | 14.1% |
| 0.24% | Mordenite | 65% | 139 | 10.5 | 1.1 | 3.4 | 20.0% | 9.9% | 5.4% | 66.5% | 18.3% |
| 0.15% | SIRAL-40 | 100% | 141 | 10.6 | 1.0 | 2.0 | 4.3% | 15.6% | 67.7% | 11.2% | 5.6% |
| 0.15% | USY (Si/Al2 = 30) | 80% | 139 | 10.4 | 1.0 | 2.0 | 9.0% | 1.3% | 0.4% | 79.1% | 19.2% |

TABLE 2-continued

Catalytic performance for the materials under study at
H2:Toluene = ~1. Performance is compared after 90-140 h on-stream.

| Pd Loading | Zeolite/Amorphous Acid | Zeolite/Acid content | T (° C.) | P (bar) | H2:Toluene (mol:mol) | WHSV (h⁻¹) | Toluene Conversion (%) | C7− (wt. %) | MCH (wt. %) | DMCHB (wt. %) | MCHT (wt. %) | C15+ (wt. %) |
|---|---|---|---|---|---|---|---|---|---|---|---|---|
| 0.15% | USY Si/Al2 = 60) | 80% | 140 | 11.2 | 1.4 | 1.6 | 18.2% | 2.3% | 0.6% | 74.7% | 22.4% | |
| 0.15% | ZSM-12 | 65% | 140 | 10.7 | 1.4 | 1.5 | 23.5% | 16.0% | 60.5% | 21.3% | 2.2% | |
| 0.24% | ZSM-12 | 65% | 139 | 10.3 | 1.0 | 2.0 | 19.1% | 15.6% | 61.6% | 20.2% | 2.5% | |
| 0.24% | ZSM-48 | 65% | 140 | 11.1 | 1.0 | 3.6 | 0.4% | 10.1% | 71.0% | 18.9% | 0.0% | |
| 0.15% | ZSM-5 | 100% | 139 | 11.2 | 1.4 | 1.5 | 1.3% | 16.7% | 66.2% | 15.4% | 1.7% | |
| 0.15% | ZSM-57 | 50% | 143 | 10.6 | 1.4 | 1.5 | 28.6% | 25.4% | 47.4% | 21.8% | 5.5% | |

TABLE 3

Catalytic performance for the materials under study at
H2:Toluene = ~2. Performance is compared after 60-90 h on-stream.

| Catalyst | | | Conditions | | | | Conversion and selectivity | | | | | |
|---|---|---|---|---|---|---|---|---|---|---|---|---|
| Pd Loading | Zeolite/Amorphous Acid | Zeolite/Acid content | T (° C.) | P (bar) | H2:Toluene (mol:mol) | WHSV (h⁻¹) | Toluene Conversion (%) | C7− (wt. %) | MCH (wt. %) | DMCHB (wt. %) | MCHT (wt. %) | C15+ (wt. %) |
| 0.15% | Beta | 80% | 141 | 10.6 | 2.0 | 2.0 | 51.1% | 0.8% | 41.8% | 0.3% | 56.7% | 0.3% |
| 0.24% | MCM-22 | 65% | 140 | 11.0 | 2.1 | 2.0 | 37.0% | 0.3% | 29.2% | 0.4% | 70.1% | 0.0% |
| 0.15% | MCM-49 | 40% | 140 | 10.1 | 2.0 | 2.0 | 11.6% | 0.7% | 21.6% | 0.2%. | 77.3% | 0.2% |
| 0.15% | MCM-49 | 60% | 140 | 10.7 | 2.0 | 2.0 | 11.2% | 0.3% | 17.2% | 0.2% | 80.9% | 1.4% |
| 0.15% | MCM-49 | 80% | 140 | 11.0 | 2.0 | 1.9 | 23.3% | 0.1% | 22.3% | 0.2% | 77.3% | 0.1% |
| 0.15% | MCM-56 | 40% | 141 | 10.8 | 2.0 | 2.0 | 29.3% | 0.3% | 29.2% | 0.1% | 70.2% | 0.2% |
| 0.15% | MCM-56 | 60% | 140 | 10.8 | 2.0 | 2.0 | 23.9% | 0.2% | 30.8% | 0.1% | 68.8% | 0.1% |
| 0.24% | MCM-56 | 60% | 140 | 10.2 | 2.1 | 1.9 | 31.7% | 0.4% | 61.3% | 0.1% | 37.9% | 0.3% |
| 0.24% | MCM-56 | 80% | 140 | 10.6 | 1.8 | 2.2 | 29.6% | 0.3% | 31.5% | 0.3% | 67.7% | 0.2% |
| 0.24% | Mordenite | 65% | 139 | 10.3 | 2.1 | 3.4 | 26.4% | 0.2% | 17.7% | 0.1% | 82.0% | 0.1% |
| 0.15% | SIR-AL-40 | 100% | 141 | 9.9 | 2.0 | 2.0 | 32.7% | 0.5% | 78.6% | 0.2% | 20.5% | 0.2% |
| 0.15% | USY (Si/Al2 = 30) | 80% | 139 | 10.3 | 2.0 | 2.0 | 13.1% | 0.6% | 27.1% | 0.2% | 70.4% | 1.7% |

TABLE 3-continued

Catalytic performance for the materials under study at
H2:Toluene = ~2. Performance is compared after 60-90 h on-stream.

| 0.15% | USY Si/Al2 = 60) | 80% | 140 | 10.7 | 2.1 | 2.0 | 24.9% | 0.6% | 28.0% | 0.1% | 71.1% | 0.2% |
|---|---|---|---|---|---|---|---|---|---|---|---|---|
| 0.15% | ZSM-12 | 65% | 141 | 10.1 | 2.0 | 2.0 | 44.2% | 0.8% | 44.5% | 0.3% | 54.4% | 0.0% |
| 0.24% | ZSM-12 | 65% | 139 | 10.2 | 2.1 | 2.0 | 37.1% | 0.7% | 37.3% | 0.2% | 61.5% | 0.3% |
| 0.24% | ZSM-48 | 65% | 140 | 11.0 | 2.0 | 3.6 | 19.0% | 2.6% | 92.0% | 0.1% | 4.3% | 0.9% |
| 0.15% | ZSM-5 | 100% | 139 | 10.7 | 2.0 | 2.0 | 14.7% | 3.7% | 85.0% | 0.1% | 10.9% | 0.3% |
| 0.15% | ZSM-57 | 50% | 143 | 10.0 | 2.0 | 2.0 | 53.9% | 0.4% | 51.4% | 0.6% | 47.6% | 0.0% |

| Catalyst | | | Conditions | | | | Conversion and selectivity | MCHT isomer distribution | | | |
|---|---|---|---|---|---|---|---|---|---|---|---|
| Pd Loading | Zeolite/ Amorphous Acid | Zeolite/ Acid content | T (° C.) | P (bar) | H2:Toluene (mol:mol) | WHSV (h$^{-1}$) | MCHT Yield (wt. %) | o,1-MCHT (wt. %) | p,1-MCHT (wt. %) | m,3-p,3-m,4-p,4 isomers (wt. %) | Other isomers (wt. %) |
| 0.15% | Beta | 80% | 141 | 10.6 | 2.0 | 2.0 | 29.0% | 21.0% | 50.6% | 24.0% | 4.5% |
| 0.24% | MCM-22 | 65% | 140 | 11.0 | 2.1 | 2.0 | 26.0% | 8.5% | 5.3% | 69.5% | 16.6% |
| 0.15% | MCM-49 | 40% | 140 | 10.1 | 2.0 | 2.0 | 8.9% | 14.5% | 8.5% | 62.1% | 14.9% |
| 0.15% | MCM-49 | 60% | 140 | 10.7 | 2.0 | 2.0 | 9.1% | 11.6% | 7.2% | 63.1% | 18.0% |
| 0.15% | MCM-49 | 80% | 140 | 11.0 | 2.0 | 1.9 | 18.0% | 2.1% | 1.1% | 73.1% | 23.7% |
| 0.15% | MCM-56 | 40% | 141 | 10.8 | 2.0 | 2.0 | 20.6% | 10.0% | 6.2% | 68.1% | 15.7% |
| 0.15% | MCM-56 | 60% | 140 | 10.8 | 2.0 | 2.0 | 16.5% | 8.8% | 4.8% | 70.3% | 16.1% |
| 0.24% | MCM-56 | 60% | 140 | 10.2 | 2.1 | 1.9 | 12.0% | 22.5% | 58.2% | 15.1% | 4.2% |
| 0.24% | MCM-56 | 80% | 140 | 10.6 | 1.8 | 2.2 | 20.1% | 8.7% | 4.5% | 70.0% | 16.7% |
| 0.24% | Mordenite | 65% | 139 | 10.3 | 2.1 | 3.4 | 21.6% | 11.3% | 7.0% | 66.1% | 15.5% |
| 0.15% | SIR-AL-40 | 100% | 141 | 9.9 | 2.0 | 2.0 | 6.7% | 15.7% | 67.3% | 11.3% | 5.8% |
| 0.15% | USY (Si/Al2 = 30) | 80% | 139 | 10.3 | 2.0 | 2.0 | 9.2% | 0.8% | 0.0% | 75.0% | 24.2% |
| 0.15% | USY Si/Al2 = 60) | 80% | 140 | 10.7 | 2.1 | 2.0 | 17.7% | 1.5% | 0.3% | 76.8% | 21.4% |
| 0.15% | ZSM-12 | 65% | 141 | 10.1 | 2.0 | 2.0 | 24.0% | 17.5% | 57.6% | 22.4% | 2.5% |
| 0.24% | ZSM-12 | 65% | 139 | 10.2 | 2.1 | 2.0 | 22.8% | 16.9% | 55.5% | 24.8% | 2.8% |
| 0.24% | ZSM-48 | 65% | 140 | 11.0 | 2.0 | 3.6 | 0.8% | 10.5% | 73.6% | 15.9% | 0.0% |
| 0.15% | ZSM-5 | 100% | 139 | 10.7 | 2.0 | 2.0 | 1.6% | 16.7% | 65.0% | 16.6% | 1.7% |
| 0.15% | ZSM-57 | 50% | 143 | 10.0 | 2.0 | 2.0 | 25.7% | 27.1% | 51.0% | 15.4% | 6.5% |

Example 2: Higher MCHT and Desired (m,3-MCHT, m,4-MCHT, p,3-MCHT, p,4-MCHT) Isomer Yield at Increasing Catalyst Zeolite Content The zeolite content of the catalyst extrudates was varied in order to control selectivity to desired and undesired products. Table 4 shows the effect of increasing zeolite loading on the hydroalkylation catalyst performance for MCM-49 and MCM-56 at constant Pd content loading. From the table, it can be observed that the overall yield to MCHT increases with zeolite content in the extrudate. This yield increase is mainly driven by higher conversion at constant selectivity to MCHT. In addition, the selectivity to desired MCHT isomers (m,3-MCHT, m,4-MCHT, p,3-

MCHT, p,4-MCHT) increases with increasing zeolite content for both MCM-49 and MCM-56 examples. As a result the desired isomer yield increases with zeolite content.

desired isomers. The net effect is that at higher Pd loading, a higher desired isomer yield is obtained at identical process conditions.

TABLE 4

Detail of the performance of the MCM-49 and MCM-56 based catalysts at increasing zeolite content.

| Catalyst | | | | Conversion, selectivity | | | MCHT isomer distribution | | | | Desired |
|---|---|---|---|---|---|---|---|---|---|---|---|
| | | | | | | | | | m,3-p,3- | | |
| Pd Loading | Zeolite/ Amorphous Acid | Zeolite/ Acid content | Dispersion (O/Pd ratio) | Toluene Conversion (%) | MCHT (wt %) | MCHT Yield (wt %) | o,1- MCHT (wt %) | p,1- MCHT (wt %) | m,4-p,4 isomers (wt %) | Other isomers (wt %) | isomer yield (wt %) |
| 140° C., 11 barg, $H_2$:Toluene 1:1 | | | | | | | | | | | |
| 0.15% | MCM-49 | 40% | 0.63 | 11.4% | 81.0% | 9.2% | 17.4% | 15.9% | 53.2% | 13.5% | 4.9% |
| 0.15% | MCM-49 | 60% | 0.94 | 12.9% | 84.4% | 10.9% | 12.6% | 7.8% | 61.5% | 18.1% | 6.7% |
| 0.15% | MCM-49 | 80% | 0.57 | 21.6% | 81.6% | 17.7% | 2.6% | 1.3% | 72.2% | 23.9% | 12.8% |
| 0.24% | MCM-56 | 60% | 0.58 | 30.1% | 37.3% | 11.2% | 22.7% | 58.9% | 14.5% | 3.9% | 1.6% |
| 0.24% | MCM-56 | 80% | 0.49 | 30.1% | 75.2% | 22.6% | 17.0% | 12.8% | 56.0% | 14.1% | 12.7% |
| 140° C., 11 barg, $H_2$:Toluene 2:1 | | | | | | | | | | | |
| 0.15% | MCM-49 | 40% | 0.63 | 11.6% | 77.3% | 8.9% | 14.5% | 8.5% | 62.1% | 14.9% | 5.5% |
| 0.15% | MCM-49 | 60% | 0.94 | 11.2% | 80.9% | 9.1% | 11.6% | 7.2% | 63.1% | 18.0% | 5.7% |
| 0.15% | MCM-49 | 80% | 0.57 | 23.3% | 77.3% | 18.0% | 2.1% | 1.1% | 73.1% | 23.7% | 13.2% |
| 0.24% | MCM-56 | 60% | 0.58 | 31.7% | 37.9% | 12.0% | 22.5% | 58.2% | 15.1% | 4.2% | 5.7% |
| 0.24% | MCM-56 | 80% | 0.49 | 29.6% | 67.7% | 20.1% | 8.7% | 4.5% | 70.0% | 16.7% | 14.1% |

Figure 6:
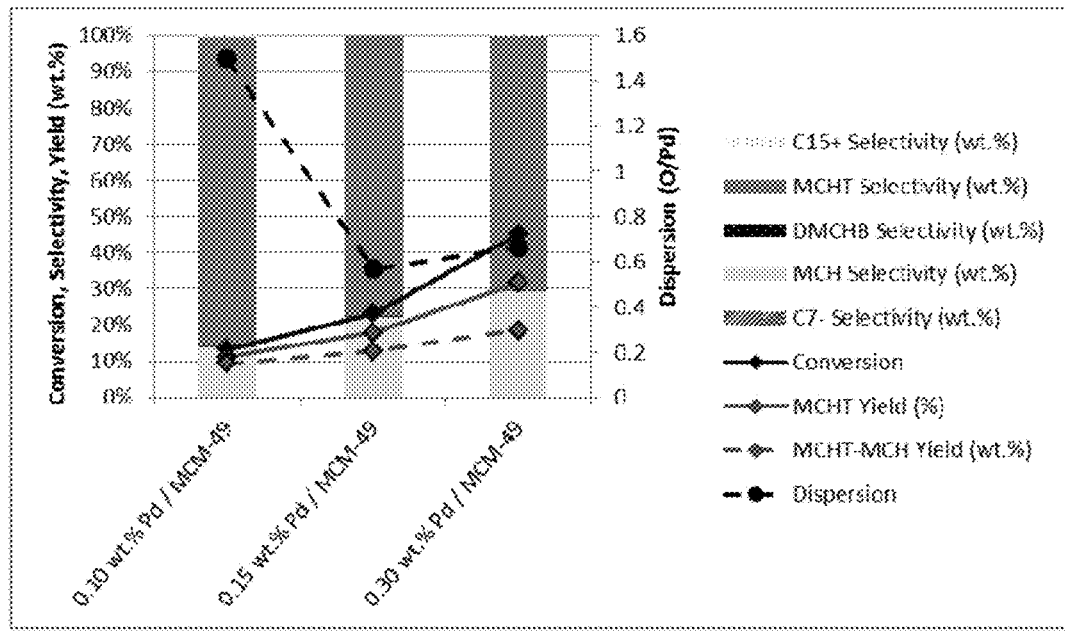
FIG. 6 is a graph of conversion and selectivity for the catalysts containing various Pd loadings at constant zeolite composition and concentration. Conditions: WHSV=2 $h^{-1}$, 140° C., 11 barg, $H_2$:Toluene=1-2.
Figure 7:
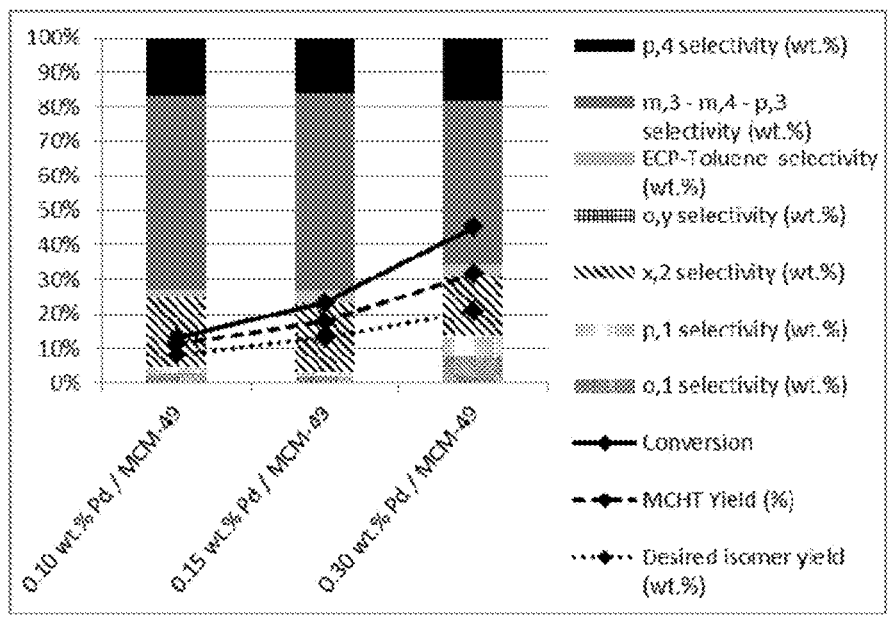
FIG. 7 is a graph of Toluene conversion, MCHT yield, desired isomer yield and isomer distribution within the MCHT fraction of the product for the catalysts containing various Pd loadings at constant zeolite composition and concentration at $H_2$:Toluene=1-2. Conditions: WHSV=2 $h^{-1}$, 140° C., 11 barg. The x, y nomenclature in the figure refer to x, y-MCHT where x=o, m, p and y=1, 2, 3, 4.

Example 3: Higher MCHT Yields and Desired Isomer Selectivity at Increasing Pd Loading The Pd metal loading of the catalysts was varied in order to increase MCHT and desired isomer (m,3-MCHT, m,4-MCHT, p,3-MCHT, p,4-MCHT) yield. The three catalysts considered in this example were 0.10 wt % Pd/MCM-49 (80 wt %), 0.15 wt % Pd/MCM-49 (80 wt %) and 0.30 wt % Pd/MCM-49 (80 wt %). Averaged data is shown for 24-300 h time-on-stream. The dispersion is expressed as O/Pd ratio from chemisorption. FIGS. 6 and 7 show the primary product selectivity and yields and the isomer MCHT distribution, respectively, for three catalysts at different Pd loading at constant zeolite content at 140° C. and 11 barg.

FIG. 6 illustrates that conversion increases with Pd loading. The dispersion of the 0.15 wt % and 0.30 wt % catalysts was comparable, while the 0.10 wt % Pd catalyst appeared to be significantly higher, with a O/Pd chemisorption ratio of higher than 1. Despite the higher Pd dispersion, the 0.10 wt % catalyst still showed significantly lower toluene conversion compared to the 0.15 wt %, indicating that dispersion does not play a large role in the activity of these catalysts in the hydroalkylation reaction. The selectivity to MCH is higher at the higher Pd content. As MCHT selectivity typically decreases with increasing toluene conversion, this may be partially due to the higher observed toluene conversion for the higher Pd content. The per-pass MCHT yield, however, is highest for the 0.30 wt % Pd catalyst. As MCH selectivity is generally undesired, the difference between MCHT and MCH yield is an important indicator and also shown in figure. The MCHT-MCH yield increases with Pd loading the considered conditions.

FIG. 7 shows the effect of Pd loading on the isomer distribution and desired isomer (m,3-MCHT, m,4-MCHT, p,3-MCHT, p,4-MCHT) yield. Even though the desired isomer contribution is less for the higher Pd loadings, the relative decrease is relatively small, indicating that there is no direct role of the Pd loading in isomer distribution and the increase in MCHT yield offsets the loss in selectivity to desired isomers. The net effect is that at higher Pd loading, a higher desired isomer yield is obtained at identical process conditions.

Figure 8:
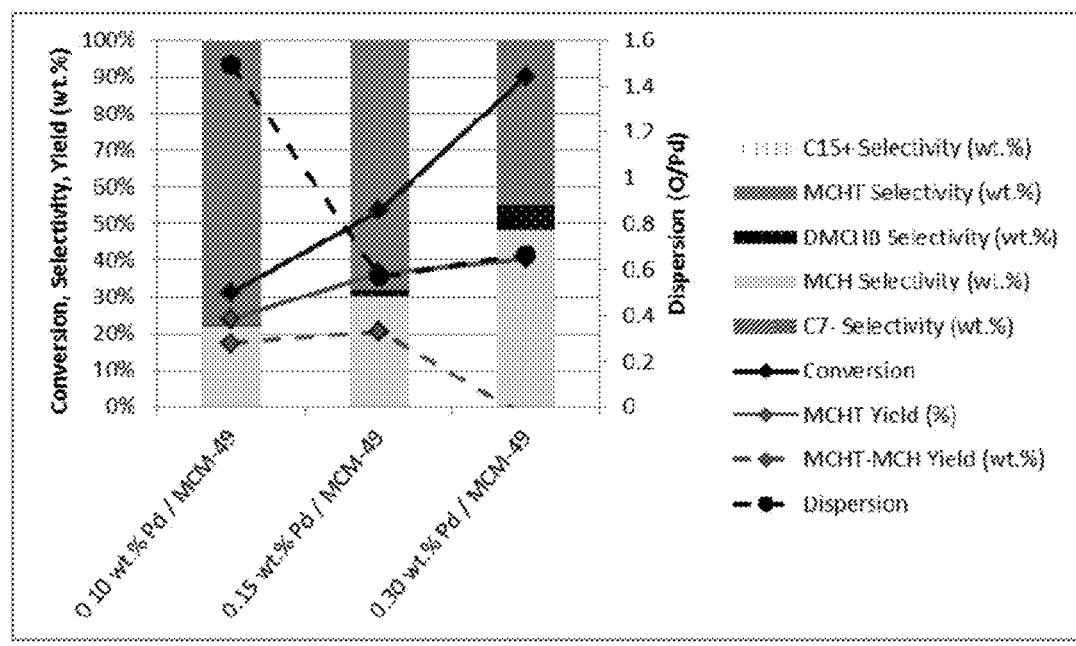
FIG. 8 is a graph of conversion and selectivity for the catalysts containing various Pd loadings at constant zeolite composition and concentration. Conditions: WHSV=2 $h^{-1}$, 160° C., 20 barg, $H_2$:Toluene=2.
Figure 9:
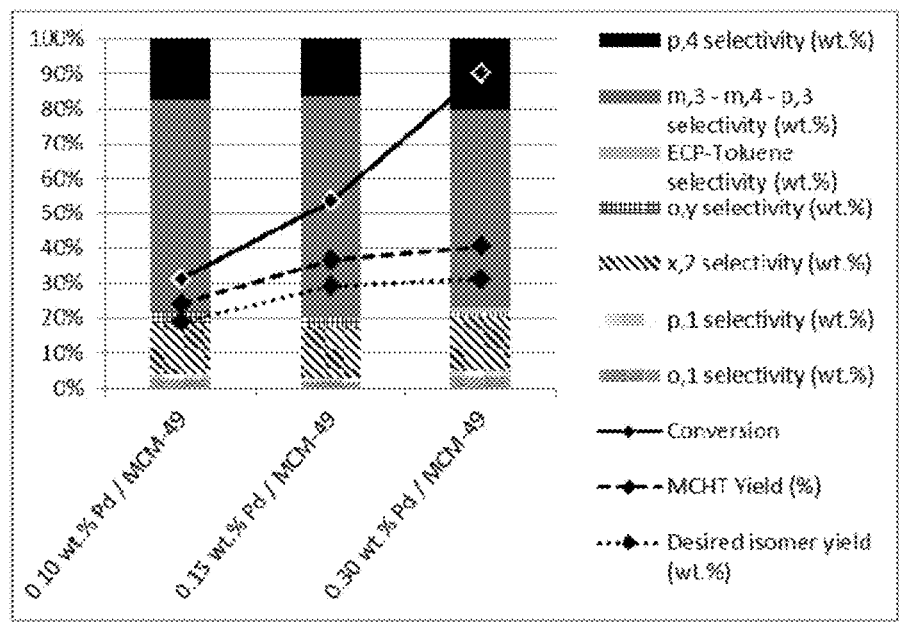
FIG. 9 is a graph of toluene conversion, MCHT yield, desired isomer yield and isomer distribution within the MCHT fraction of the product for the catalysts containing various Pd loadings at constant zeolite composition and concentration at $H_2$:Toluene=2. Conditions: WHSV=2 $h^{-1}$, 160° C., 20 barg. The x, y nomenclature in the figure refer to x, y-MCHT where x=o, m, p and y=1, 2, 3, 4.

FIGS. 8 and 9 show the average performance data at 160° C. and 20 barg and 24-300 h time-on-stream. As shown in FIG. 8, the results are similar to those obtained at 140° C. and MCHT yield increases at higher Pd loadings and otherwise constant composition. The MCH yield and DMBCH selectivity, however, also increases dramatically and as a result, the MCHT-MCH yield is close to zero for the 0.30 wt % Pd catalyst. Clearly, for the highest Pd loading at the more severe conditions, overhydrogenation of toluene and MCHT to MCH and DMBCH, respectively, occurs at much higher rates.

FIG. 9 shows, that despite the higher hydrogenation rates and resulting losses of toluene to MCH, at the more severe 160° C. and 20 barg conditions, the net desired isomer yield is close to 30% and therefore still the highest for the highest Pd loading. It is also noted that the desired isomer content appears to be more constant or slightly increasing at higher Pd loadings at 160° C. compared to the decrease with Pd loading at 140° C. This may indicate that MCHT isomerization is more significant at the higher temperature conditions.

Example 4: Higher MCHT Yields and Desired Isomer Selectivity at Higher Severity Conditions In this example, Pd/MCM-49 hydroalkylation catalysts with a zeolite content of 80 wt % and Pd loading ranging from 0.10-0.30 wt % were further examined at various conditions. The three catalysts considered in this example were 0.10 wt % Pd/MCM-49 (80 wt %), 0.15 wt % Pd/MCM-49 (80 wt %) and 0.30 wt % Pd/MCM-49 (80 wt %).

TABLE 5

Impact of process conditions on Pd/ MCM-49 catalyst performance

| Catalyst (Pd/MCM-49) | | | | | | Conversion, Selectivity, Yield | | | | | | | |
|---|---|---|---|---|---|---|---|---|---|---|---|---|---|
| | | Conditions | | | | | | MCHT | MCHT Isomer Distribution | | | | |
| Pd Loading | Dispersion (O/Pd ratio) | T (° C.) | P (barg) | Molar H₂:Toluene ratio | WHSV (g h⁻¹) | Toluene Conversion (%) | MCHT (wt %) | MCHT Yield (wt %) | Yield − MCH Yield (wt %) | o,1- MCHT (wt %) | p,1- MCHT (wt %) | m,3-p,3- m,4-p,4 isomers (wt %) | Other isomers (wt %) | Desired Isomer Yield (%) |
| 0.10% | 1.50 | 137 | 10.9 | 1.0 | 2.0 | 12.8% | 86.0% | 11.0% | 9.3% | 3.7% | 1.8% | 72.7% | 21.8% | 8.0% |
| 0.10% | 1.50 | 137 | 9.9 | 2.0 | 2.0 | 13.3% | 85.2% | 11.3% | 9.5% | 3.0% | 1.5% | 72.8% | 22.8% | 8.2% |
| 0.10% | 1.50 | 157 | 19.2 | 1.0 | 2.0 | 25.4% | 81.4% | 20.7% | 16.2% | 3.1% | 7.3% | 60.4% | 29.2% | 12.5% |
| 0.10% | 1.50 | 157 | 19.2 | 2.1 | 1.9 | 31.1% | 77.4% | 24.1% | 17.3% | 2.5% | 1.3% | 78.4% | 17.8% | 18.9% |
| 0.15% | 0.57 | 139 | 10.9 | 1.0 | 2.0 | 21.9% | 80.3% | 17.6% | 13.4% | 2.7% | 1.3% | 72.9% | 23.1% | 12.8% |
| 0.15% | 0.57 | 139 | 11.0 | 2.0 | 1.9 | 23.3% | 77.3% | 18.0% | 12.8% | 2.1% | 1.1% | 73.1% | 23.7% | 13.2% |
| 0.15% | 0.57 | 158 | 19.9 | 1.0 | 1.9 | 53.2% | 70.6% | 37.5% | 22.7% | 1.9% | 0.8% | 71.8% | 25.5% | 26.9% |
| 0.15% | 0.57 | 158 | 19.9 | 2.0 | 2.0 | 53.6% | 68.2% | 36.5% | 20.5% | 1.8% | 0.9% | 79.8% | 17.5% | 29.2% |
| 0.30% | 0.66 | 139 | 10.0 | 1.0 | 2.0 | 45.9% | 71.2% | 32.7% | 19.9% | 7.1% | 5.1% | 67.4% | 20.4% | 22.0% |
| 0.30% | 0.66 | 139 | 10.0 | 2.0 | 2.0 | 46.4% | 72.2% | 33.5% | 21.0% | 6.7% | 5.0% | 67.3% | 21.0% | 22.5% |
| 0.30% | 0.66 | 158 | 19.1 | 1.0 | 2.0 | 65.7% | 64.2% | 42.2% | 20.2% | 1.5% | 2.4% | 78.2% | 17.9% | 33.0% |
| 0.30% | 0.66 | 158 | 19.1 | 2.0 | 2.0 | 89.7% | 47.8% | 42.9% | −4.1% | 2.8% | 1.6% | 76.5% | 19.0% | 32.8% |

Table 5 summarizes the results for the three catalysts at the various tested conditions ranging from 140-160° C. and H₂:toluene ratio 1-2 at WHSV=2 h⁻¹ on a toluene basis. The table shows that, in general, at 160° C. and 20 barg, the MCHT yield is higher for all considered catalysts. For the 0.10 wt % and 0.15 wt % Pd catalysts, the selectivity and yield to desired (m,3-MCHT, m,4-MCHT, p,3-MCHT, p,4-MCHT) isomers is highest at a molar H₂:toluene ratio of 2 and 160° C. The 0.30 wt % Pd catalyst, on the other hand, loses selectivity to MCH at these conditions and the selectivity and yield to desired isomers is at a maximum for a molar H₂:toluene ratio of 1 at 160° C. The loss in selectivity to MCH is more clearly resolved when the MCHT yield–MCH yield spread is calculated. In the case of the 0.30 wt % Pd catalyst, this parameter is −4.1% at the highest temperature and H₂:toluene ratio=1.

In general, H₂:toluene ratio of 1 and a reaction temperature of 160° C. at 20 barg appears to give the best overall MCHT and desired isomer yield at minimal MCH yield. For the lower Pd loadings, higher H₂:toluene ratios give slightly enhanced performance.

Example 5: Assessment of Other Metals as Hydroalkylation Catalysts

In this example, the performance of Pd catalysts in the hydroalkylation reaction is compared to other metals. The considered materials consisted of catalysts containing various concentrations of a MWW family zeolite phase (MCM-22, MCM-49 or MCM-56) at various weight loadings of Co, Ni, Pd, Pt, Re and Ru.

Figure 10:
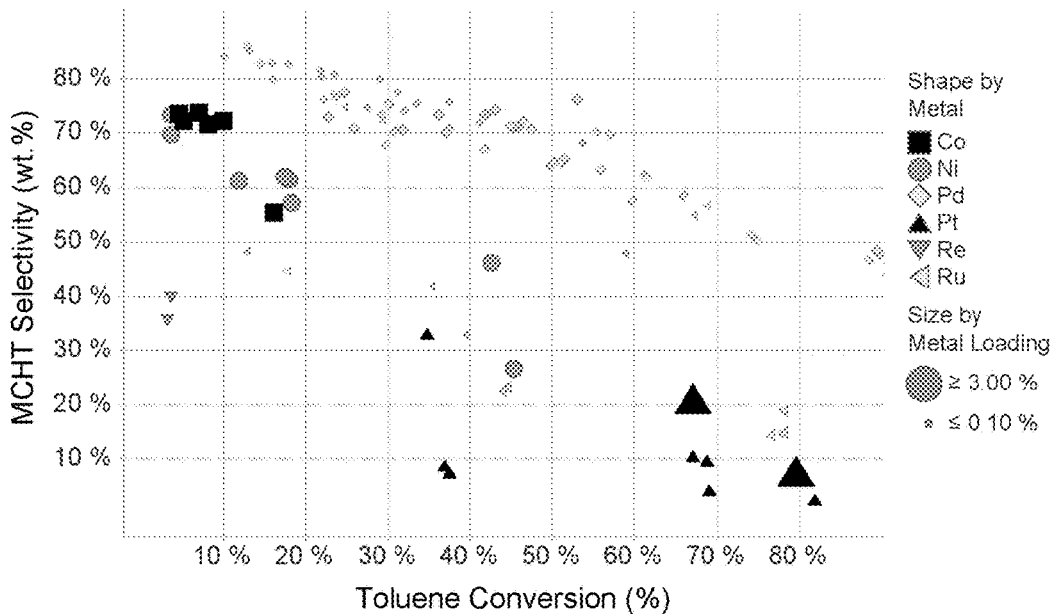
FIG. 10 is a graph of MCHT selectivity as a function of conversion for MWW (MCM-22, MCM-49, MCM-56) family catalysts containing various metals at various loadings. Data shown for WHSV=2 $h^{-1}$, $H_2$:Toluene ratio=1-2, T=140-160° C.

FIG. 10 shows a summary of the obtained results for the materials containing different metals. In general, the Pd-based catalysts show superior MCHT selectivity for each conversion as compared to the other metals.

Figure 11:
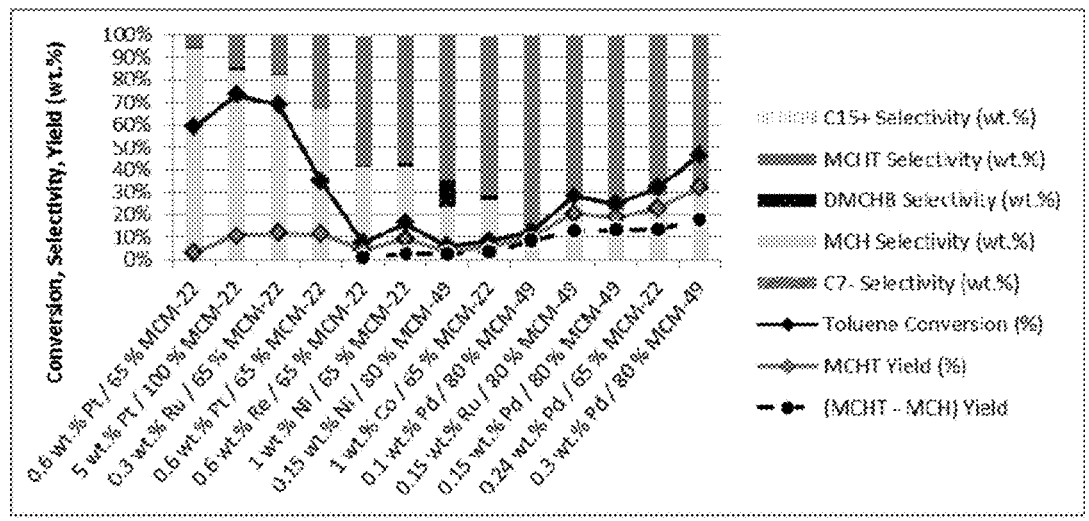
FIG. 11 is a graph of conversion and selectivity for the MWW family catalysts containing various metal functions at various concentrations. Conditions: WHSV=2 $h^{-1}$, 140° C., 11 barg, $H_2$:Toluene=1-2.

FIG. 11 shows the conversion, MCHT yield and selectivity plot for all considered materials. In general, Pd-based materials show superior performance in terms of MCHT yield over all other considered materials. Ni, Pt and Ru-based catalysts generally show very high selectivity to MCH, suggesting that the metals tend to over-hydrogenate the toluene substrate. Re and Co-based catalysts showed very low activity over the considered range of conditions. One specific Ru-based catalyst showed generally good performance in terms of MCHT selectivity and yield, suggesting that at high (80 wt %) zeolite content, similar performance to Pd-based catalysts might be obtained. Co-based catalysts also showed reasonable selectivity to MCHT, albeit at low conversion. Ni-based catalysts show somewhat higher conversion compared to Co-based catalyst, but at ~20-30% lower MCHT selectivity compared to Pd-based catalysts. The difference in MCH and MCHT yield is very good for the Pd based catalysts.

Figure 12:
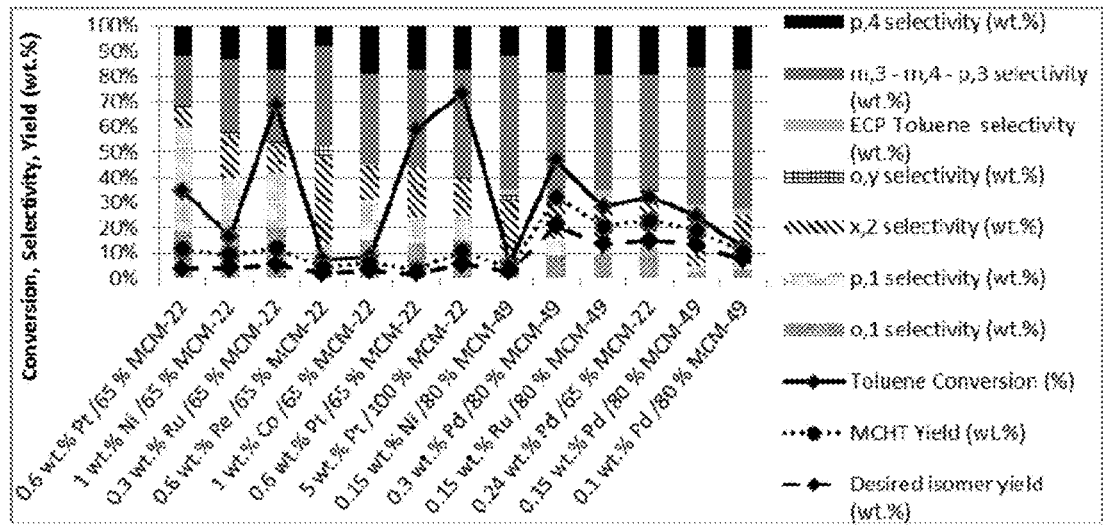
FIG. 12 is a graph of toluene conversion, MCHT yield, desired isomer yield and isomer selectivity within the MCHT fraction (bars). Conditions: WHSV=2 $h^{-1}$, 140° C., 11 barg, $H_2$:Toluene=1-2. The x, y nomenclature in the figure refers to x, y-MCHT where x=o, m, p and y=1, 2, 3, 4.
Figure 13:
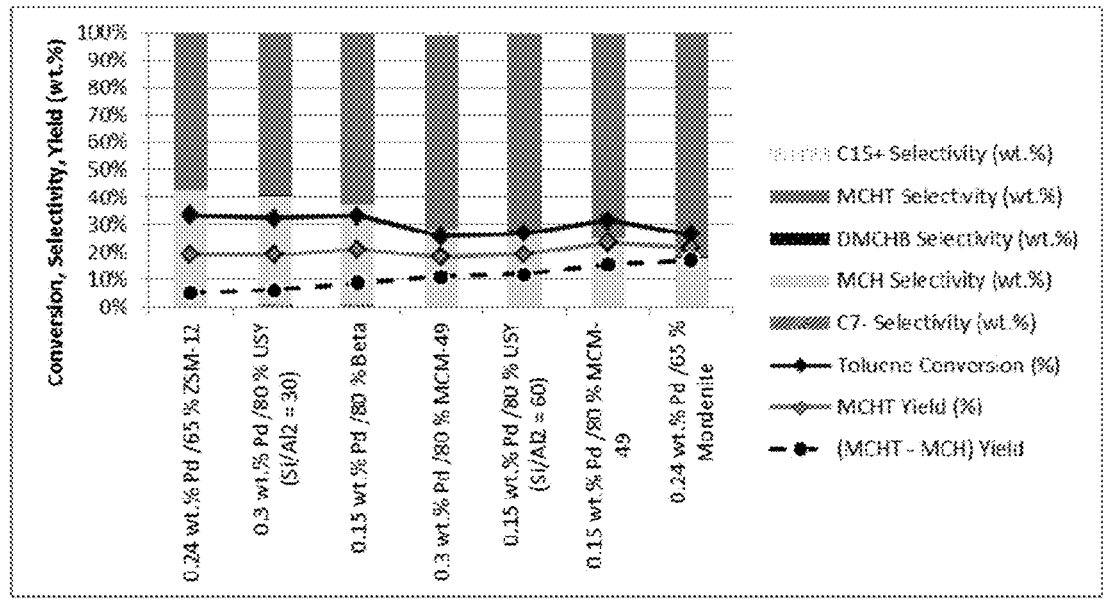
FIG. 13 is a graph for Example 1 showing the selectivity, MCHT yield and the difference between MCHT and MCH yield for the catalysts containing 12 membered ring zeolite functions at various concentrations at comparable toluene conversion (25-35%). Conditions: WHSV=~2 $h^{-1}$, 140° C., 11 barg, $H_2$:Toluene=1-2.
Figure 14:
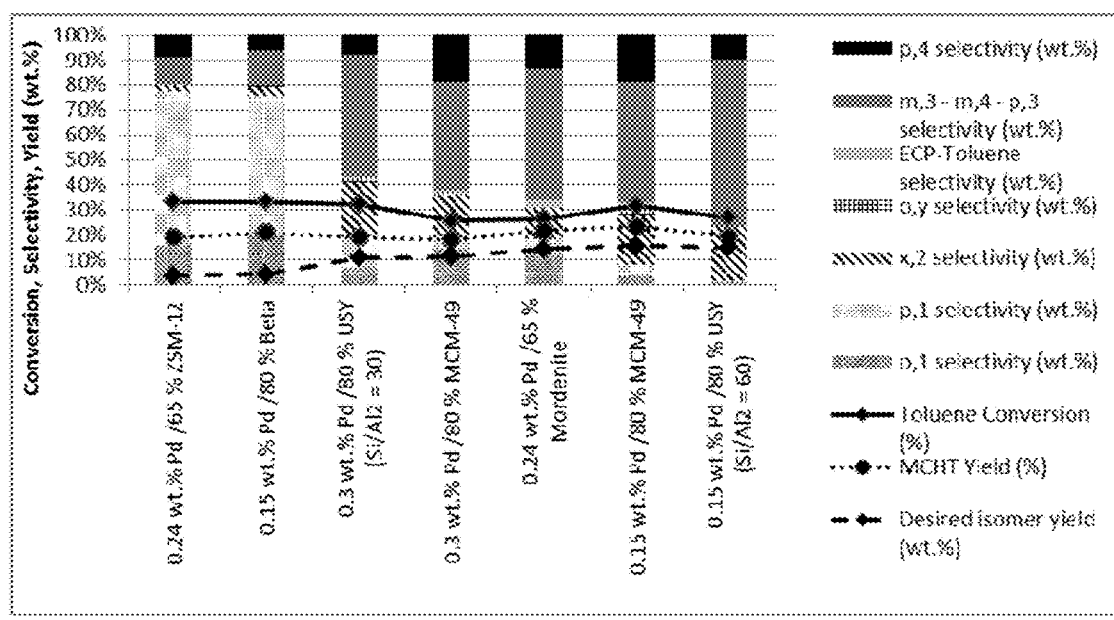
FIG. 14 is a graph for Example 1 showing MCHT yield, desired isomer yield and isomer selectivity within the MCHT fraction (bars) of the product for the catalysts containing 12 membered ring zeolite functions at various concentrations at comparable toluene conversion (25-35%). Conditions: WHSV=~2 $h^{-1}$, 140° C., 11 barg, $H_2$:Toluene=1-2. The x, y nomenclature in the figure refer to x, y-MCHT where x=o, m, p and y=1, 2, 3, 4.

FIG. 12 shows that the MCHT isomer distribution is rather constant for the different metals, once again suggesting that the isomer distribution is mainly controlled by the zeolite phase and not the metal type and loading.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

The invention claimed is:

1. A process for producing (methylcyclohexyl)toluene, the process comprising:
   (a) contacting a feed comprising toluene with hydrogen in the presence of a hydroalkylation catalyst under conditions effective to produce a hydroalkylation reaction product comprising (methylcyclohexyl)toluene, wherein the hydroalkylation catalyst comprises: 1) binder present at 40 wt % or less based upon weight of final catalyst composition, 2) a hydrogenation component present at 0.2 wt % or less based upon weight of final catalyst composition, and 3) an acidic component comprising a molecular sieve having a twelve membered or higher ring pore opening, channel or pocket and a largest pore dimension of 6.0 angstroms or more present at 60 wt % or more, based upon weight of final catalyst composition, wherein the hydrogenation component of the hydroalkylation catalyst is selected from the group consisting of palladium, ruthenium, nickel, zinc, tin, cobalt and compounds and mixtures thereof, and wherein the hydroalkylation reaction product comprises at least 60 wt % of the m,3, m,4, p,3 and p,4-isomers of (methylcyclohexyl)toluene based on the total weight of all the (methylcyclohexyl)toluene isomers, and less than 30 wt % of methylcyclohexane.

2. The process of claim 1, further comprising producing methyl-substituted biphenyl compounds, the process further comprising:
(b) dehydrogenating at least part of the hydroalkylation reaction product in the presence of a dehydrogenation catalyst under conditions effective to produce a dehydrogenation reaction product comprising a mixture of methyl-substituted biphenyl compounds.

3. The process of claim 2, further comprising producing biphenyl carboxylic acids, the process further comprising:
(c) contacting at least part of the dehydrogenation reaction product with an oxidizing gas under conditions effective to convert at least part of the methyl-substituted biphenyl compounds to biphenyl carboxylic acids.

4. The process of claim 3, further comprising producing biphenyl esters, the process further comprising:
(d) reacting the biphenyl carboxylic acids with one or more $C_1$ to $C_3$ alcohols under conditions effective to produce biphenyl esters.

5. The process of claim 1, wherein the molecular sieve is selected from the group consisting of ZSM-12, zeolite Beta, faujasite, mordenite, and mixtures thereof.

6. The process of claim 1, wherein the molecular sieve is selected from the group consisting of zeolite Y, Ultrastable Y (USY), Dealuminated Y (Deal Y), mordenite and mixtures thereof.

7. The process of claim 1, wherein the molecular sieve does not comprise a molecular sieve of the MCM-22 family.

8. The process of claim 1, wherein the binder component of the hydroalkylation catalyst is selected from pseudoboehmite alumina, alumina, silica, titania and mixtures thereof.

9. The process of claim 1, wherein the molar ratio of hydrogen to feed supplied to the contacting (a) is from about 0.15:1 to about 15:1.

10. The process of claim 1, wherein the hydroalkylation reaction product comprises less than 5 wt % of compounds having a methyl group at the 1 position.

11. The process of claim 1, wherein the feed further comprises benzene and/or at least one alkylbenzene different from toluene.

12. The process of claim 2, wherein the dehydrogenation catalyst comprises an element or compound thereof selected from Group 10 of the Periodic Table of Elements.

13. The process of claim 2, wherein the dehydrogenation conditions in (b) include a temperature from about 200° C. to about 600° C. and a pressure from about 100 kPa to about 3550 kPa.

14. The process of claim 1, wherein the conditions in the contacting (a) include a temperature from about 100° C. to about 400° C. and a pressure from about 100 to about 7,000 kPa.

15. The process of claim 1, wherein the feed consists essentially of toluene.

16. The process of claim 3, further comprising producing biphenyl esters, the process further comprising:
(d) reacting the biphenyl carboxylic acids with one or more $C_1$ to $C_{14}$ OXO-alcohols under conditions effective to produce biphenyl esters.

17. The process of claim 16, where the OXO-alcohol is branched.

18. The process of claim 16, where the OXO-alcohol has an average branching of from 0.2 to 5.0 branches per molecule.

19. The process of claim 16, where the OXO-alcohol has 0.35 to 5.0 methyl branches per molecule.

20. The process of claim 1, wherein the molecular sieve is selected from the group consisting of ZSM-12, zeolite Beta, faujasite, mordenite, zeolite Y, Ultrastable Y (USY), Dealuminated Y (Deal Y), mordenite and mixtures thereof.

21. The process of claim 1, wherein the hydrogenation component of the hydroalkylation catalyst comprises palladium.

* * * * *